United States Patent
Igawa et al.

(10) Patent No.: US 12,168,697 B2
(45) Date of Patent: Dec. 17, 2024

(54) BISPECIFIC ANTIBODIES WHICH BIND BLOOD COAGULATION FACTOR VIII AND HAVE ENHANCED ACTIVITY, AND METHODS OF USE THEREOF FOR TREATING BLEEDING AND ASSOCIATED CONDITIONS

(71) Applicant: Chugai Seiyaku Kabushiki Kaisha, Tokyo (JP)

(72) Inventors: Tomoyuki Igawa, Shizuoka (JP); Yuri Teranishi, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 17/563,149

(22) Filed: Dec. 28, 2021

(65) Prior Publication Data

US 2022/0119551 A1    Apr. 21, 2022

Related U.S. Application Data

(62) Division of application No. 16/061,429, filed as application No. PCT/JP2016/088299 on Dec. 22, 2016, now abandoned.

(30) Foreign Application Priority Data

Dec. 25, 2015    (JP) .................................. 2015-253324

(51) Int. Cl.
C07K 16/36    (2006.01)

(52) U.S. Cl.
CPC ........ *C07K 16/36* (2013.01); *C07K 2317/526* (2013.01); *C07K 2317/53* (2013.01)

(58) Field of Classification Search
CPC .............. C07K 16/36; C07K 2317/526; C07K 2317/53
See application file for complete search history.

(56) References Cited

U.S. PATENT DOCUMENTS

| | | | |
|---|---|---|---|
| 4,208,479 A | 6/1980 | Maggio et al. |
| 4,444,878 A | 4/1984 | Paulus |
| 4,474,893 A | 10/1984 | Reading |
| 5,496,549 A | 3/1996 | Yamazaki et al. |
| 5,591,828 A | 1/1997 | Bosslet et al. |
| 5,693,762 A | 12/1997 | Queen et al. |
| 5,744,446 A | 4/1998 | Lollar et al. |
| 6,005,091 A | 12/1999 | Blackburn et al. |
| 6,010,902 A | 1/2000 | Ledbetter et al. |
| 7,018,632 B2 | 3/2006 | Lindhofer et al. |
| 7,033,590 B1 | 4/2006 | Scheiflinger et al. |
| 7,538,196 B2 | 5/2009 | Jung |
| 7,691,380 B2 | 4/2010 | Thorpe et al. |
| 7,732,149 B2 | 6/2010 | Kojima et al. |
| 8,030,461 B2 | 10/2011 | Kojima |
| 8,062,635 B2 | 11/2011 | Hattori et al. |
| 8,337,841 B2 | 12/2012 | Kojima et al. |
| 8,765,124 B2 | 7/2014 | Saito et al. |
| 9,334,331 B2 | 5/2016 | Igawa et al. |
| 10,022,319 B2 | 7/2018 | Igawa et al. |
| 10,450,381 B2 | 10/2019 | Igawa et al. |
| 10,759,870 B2 | 9/2020 | Teranishi et al. |
| 2002/0062010 A1 | 5/2002 | Arathoon et al. |
| 2003/0207346 A1 | 11/2003 | Arathoon et al. |
| 2005/0266425 A1 | 12/2005 | Zauderer et al. |
| 2007/0041978 A1 | 2/2007 | Hattori et al. |
| 2007/0244301 A1 | 10/2007 | Siekmann et al. |
| 2008/0075712 A1 | 3/2008 | Hattori et al. |
| 2009/0324589 A1 | 12/2009 | Igawa et al. |
| 2010/0003254 A1 | 1/2010 | Hattori et al. |
| 2010/0285011 A1 | 11/2010 | Morichika et al. |
| 2012/0237517 A1 | 9/2012 | Hattori et al. |
| 2013/0018174 A1 | 1/2013 | Igawa et al. |
| 2013/0330345 A1 | 12/2013 | Igawa et al. |
| 2014/0037632 A1 | 2/2014 | Igawa et al. |
| 2014/0370018 A1 | 12/2014 | Igawa et al. |
| 2014/0370020 A1 | 12/2014 | Kuramochi et al. |
| 2015/0315296 A1 | 11/2015 | Schaefer et al. |
| 2016/0222129 A1 | 8/2016 | Igawa et al. |
| 2017/0022293 A1 | 1/2017 | Igawa et al. |
| 2017/0145111 A1 | 5/2017 | Hattori et al. |
| 2017/0253663 A1 | 9/2017 | Yoneyama |
| 2018/0002443 A1 | 1/2018 | Hattori et al. |
| 2018/0244800 A1 | 8/2018 | Hattori et al. |
| 2018/0344630 A1 | 12/2018 | Igawa et al. |

(Continued)

FOREIGN PATENT DOCUMENTS

| CA | 2019559 | 1/2002 |
|---|---|---|
| CA | 2603264 | 10/2006 |

(Continued)

OTHER PUBLICATIONS

Paul, WE (1993) Fundamental Immunology, 3rd ed. Raven Press, NY, Chap. 9, pp. 292-295.*
Rudikoff, S et al. (1982) Proc. Natl. Acad. Sci. USA, 79:1979-1983 (doi: 10.1073/pnas.79.6.1979).*
Colman, PM (1994) Research in Immunology, Elsevier, NY, 145(1):33-36.*
Bendig M. M. (1995) Methods: A Companion to Methods in Enzymology, 8:83-93.*
MacCallum et al. (Oct. 11, 1996) J. Mol. Biol., 262(5):732-745. (doi: 10.1006/jmbi.1996.0548).*
Casset et al (2003) Biochemical and Biophysical Research Communications, 307:198-205. (doi:10.1016/S0006-291X(03)01131-8).*
Chen et al. (1995) EMBO J., 14(12):2784-2794. (doi: 10.1002/j.1460-2075.1995.tb07278.x).*

(Continued)

*Primary Examiner* — Robert S Landsman
(74) *Attorney, Agent, or Firm* — Fish & Richardson P.C.

(57) ABSTRACT

As a result of producing ACE910 variants in which various sites of the constant regions were modified, the inventors discovered bispecific antibodies having FVIII mimetic activity higher than that of ACE910. The inventors also identified mutation positions that elevate the FVIII mimetic activity and discovered methods for elevating the FVIII mimetic activity by using the mutations.

16 Claims, 5 Drawing Sheets

Specification includes a Sequence Listing.

(56) References Cited

U.S. PATENT DOCUMENTS

| | | |
|---|---|---|
| 2019/0112390 A1 | 4/2019 | Hattori et al. |
| 2019/0185578 A1 | 6/2019 | Igawa et al. |
| 2019/0194352 A1 | 6/2019 | Yoneyama et al. |
| 2019/0315884 A1 | 10/2019 | Igawa et al. |
| 2019/0359728 A1 | 11/2019 | Hattori et al. |
| 2020/0087380 A1 | 3/2020 | Kuramochi et al. |
| 2020/0223940 A1 | 7/2020 | Teranishi et al. |
| 2020/0270363 A1 | 8/2020 | Igawa et al. |
| 2020/0277402 A1 | 9/2020 | Hattori et al. |
| 2020/0283544 A1 | 9/2020 | Hosoguchi et al. |
| 2020/0354473 A1 | 11/2020 | Teranishi et al. |
| 2021/0107994 A1 | 4/2021 | Shima et al. |
| 2021/0107995 A1 | 4/2021 | Hattori et al. |
| 2021/0189006 A1 | 6/2021 | Saeki et al. |
| 2021/0380717 A1 | 12/2021 | Hattori et al. |
| 2022/0073644 A1 | 3/2022 | Igawa et al. |
| 2022/0073645 A1 | 3/2022 | Yoneyama |
| 2022/0213217 A1 | 7/2022 | Hattori et al. |
| 2022/0267470 A1 | 8/2022 | Igawa et al. |
| 2023/0152280 A1 | 5/2023 | Sato et al. |
| 2023/0212315 A1 | 7/2023 | Igawa et al. |
| 2023/0348621 A1 | 11/2023 | Hattori et al. |
| 2024/0052059 A1 | 2/2024 | Shima et al. |
| 2024/0059795 A1 | 2/2024 | Igawa et al. |

FOREIGN PATENT DOCUMENTS

| | | |
|---|---|---|
| CA | 2812739 A | 10/2012 |
| CA | 2859667 A | 6/2013 |
| CA | 2888496 A | 5/2014 |
| CA | 3027018 A | 1/2018 |
| CA | 3031082 | 1/2018 |
| CA | 2603408 C | 8/2018 |
| CN | 101883588 | 11/2010 |
| CN | 102858366 | 1/2013 |
| CN | 103298937 | 9/2013 |
| EP | 0 369 566 | 5/1990 |
| EP | 0 404 097 | 9/1996 |
| EP | 0 979 281 | 2/2000 |
| EP | 1 327 681 | 7/2003 |
| EP | 1 693 448 | 8/2006 |
| EP | 1 220 923 | 6/2007 |
| EP | 1 876 236 | 1/2008 |
| EP | 1 505 148 | 4/2009 |
| EP | 1 605 058 | 5/2009 |
| EP | 1 688 488 | 8/2011 |
| EP | 1 688 488 B9 | 3/2012 |
| EP | 2 238 985 | 8/2012 |
| EP | 2 526 963 | 11/2012 |
| EP | 2 644 698 | 10/2013 |
| EP | 3 395 835 B | 2/2021 |
| JP | H02-145187 | 6/1990 |
| JP | H05-184383 | 7/1993 |
| JP | H05-199894 | 8/1993 |
| JP | H05-203652 | 8/1993 |
| JP | H05-213775 | 8/1993 |
| JP | H05-304992 | 11/1993 |
| JP | H06-104071 | 12/1994 |
| JP | H08-510555 | 11/1996 |
| JP | H10-165184 | 6/1998 |
| JP | H10-511085 | 10/1998 |
| JP | H11-71288 | 3/1999 |
| JP | H11-504007 | 4/1999 |
| JP | H11-506310 | 6/1999 |
| JP | 3032287 | 4/2000 |
| JP | 2001-523971 | 11/2001 |
| JP | 2002-518041 | 6/2002 |
| JP | 2003-055398 | 2/2003 |
| JP | 2003-509049 | 3/2003 |
| JP | 2008-510466 | 4/2008 |
| JP | 2011-502126 | 1/2011 |
| JP | 2011-137000 | 7/2011 |
| JP | 2014-511836 | 5/2014 |
| JP | 2014-524748 | 9/2014 |
| JP | 2015-502409 | 1/2015 |
| JP | 2015-504434 | 2/2015 |
| JP | 2015-514684 | 5/2015 |
| JP | 2015-536349 | 12/2015 |
| JP | 2016-508117 | 3/2016 |
| JP | 2017-511139 | 4/2017 |
| KR | 2013/0102113 | 9/2013 |
| KR | 2013/0102640 | 9/2013 |
| NO | 20062087 | 7/2006 |
| RU | 2339696 | 11/2008 |
| TW | 2007/14313 | 4/2007 |
| TW | I452135 | 9/2014 |
| TW | I452136 | 9/2014 |
| TW | 2016/00112 | 1/2016 |
| WO | WO 91/08770 | 6/1991 |
| WO | WO 93/11161 | 6/1993 |
| WO | WO 94/13804 | 6/1994 |
| WO | WO 95/01571 | 1/1995 |
| WO | WO 96/01653 | 1/1996 |
| WO | WO 96/07754 | 3/1996 |
| WO | WO 96/16673 | 6/1996 |
| WO | WO 96/26964 | 9/1996 |
| WO | WO 96/27011 | 9/1996 |
| WO | WO 96/33208 | 10/1996 |
| WO | WO 98/50431 | 11/1998 |
| WO | WO 99/10494 | 4/1999 |
| WO | WO 99/67359 | 12/1999 |
| WO | WO 01/19992 | 3/2001 |
| WO | WO 01/90192 | 11/2001 |
| WO | WO 02/06838 | 1/2002 |
| WO | WO 02/30463 | 4/2002 |
| WO | WO 02/33073 | 4/2002 |
| WO | WO 03/35835 | 1/2003 |
| WO | WO 03/42231 | 5/2003 |
| WO | WO 03/87163 | 10/2003 |
| WO | WO 03/91424 | 11/2003 |
| WO | WO 2004/009618 | 1/2004 |
| WO | WO 2004/060919 | 7/2004 |
| WO | WO 2004/065611 | 8/2004 |
| WO | WO 2004/097041 | 11/2004 |
| WO | WO 2004/111233 | 12/2004 |
| WO | WO 2005/025615 | 3/2005 |
| WO | WO 2005/035753 | 4/2005 |
| WO | WO 2005/035754 | 4/2005 |
| WO | WO 2005/035756 | 4/2005 |
| WO | WO 2006/031370 | 3/2006 |
| WO | WO 2006/106905 | 10/2006 |
| WO | WO 2006/109592 | 10/2006 |
| WO | WO 2007/114319 | 10/2007 |
| WO | WO 2007/114325 | 10/2007 |
| WO | WO 2007/147901 | 12/2007 |
| WO | WO 2009/041643 | 4/2009 |
| WO | WO 2009/058492 | 5/2009 |
| WO | WO 2009/084659 | 7/2009 |
| WO | WO 2009/089004 | 7/2009 |
| WO | WO 2010/129304 | 11/2010 |
| WO | WO 2011/090088 | 2/2011 |
| WO | WO 2011/078332 | 6/2011 |
| WO | WO 2012/067176 | 5/2012 |
| WO | WO 2012/131555 | 10/2012 |
| WO | WO 2013/011076 | 1/2013 |
| WO | WO 2013/065708 | 5/2013 |
| WO | WO 2013/076186 | 5/2013 |
| WO | WO 2013/096291 | 6/2013 |
| WO | WO 2013/124451 | 8/2013 |
| WO | WO 2013/131866 | 9/2013 |
| WO | WO 2014/081955 | 5/2014 |
| WO | WO 2014/082179 | 6/2014 |
| WO | WO 2015/134894 | 9/2015 |
| WO | WO 2015/150447 | 10/2015 |
| WO | WO 2015/175874 | 11/2015 |
| WO | WO 2015/181805 | 12/2015 |
| WO | WO 2015/194233 | 12/2015 |
| WO | WO 2016/001810 | 1/2016 |
| WO | WO 2016/164708 | 10/2016 |
| WO | WO 2016/166014 | 10/2016 |
| WO | WO 2016/171202 | 10/2016 |
| WO | WO 2017/110980 | 6/2017 |
| WO | WO 2017/129585 | 8/2017 |
| WO | WO 2017/188356 | 11/2017 |

(56) References Cited

FOREIGN PATENT DOCUMENTS

| WO | WO 2017/205014 | 11/2017 |
|---|---|---|
| WO | WO 2018/016881 | 1/2018 |
| WO | WO 2018/021450 | 2/2018 |
| WO | WO 2018/181870 | 10/2018 |
| WO | WO 2019/065795 | 4/2019 |
| WO | WO 2019/088143 | 5/2019 |
| WO | WO 2021/201202 | 10/2021 |

OTHER PUBLICATIONS

U.S. Appl. No. 14/921,590, filed Oct. 23, 2015, Hattori et al.
U.S. Appl. No. 15/172,727, filed Jun. 3, 2016, Hattori et al.
U.S. Appl. No. 15/963,345, filed Apr. 26, 2018, Hattori et al.
U.S. Appl. No. 16/093,495, filed Oct. 12, 2018, Saeki et al.
U.S. Appl. No. 16/099,341, filed Nov. 6, 2018, Ternashi et al.
U.S. Appl. No. 16/226,798, filed Dec. 20, 2018, Hattori et al.
U.S. Appl. No. 16/459,791, filed Jul. 2, 2019, Igawa et al.
U.S. Appl. No. 16/496,089, filed Sep. 20, 2019, Shima et al.
U.S. Appl. No. 16/536,385, filed Aug. 9, 2019, Hattori et al.
U.S. Appl. No. 16/825,513, filed Mar. 20, 2020, Hattori et al.
U.S. Appl. No. 16/936,575, filed Jul. 23, 2020, Teranishi et al.
U.S. Appl. No. 17/130,736, filed Dec. 22, 2020, Hattori et al.
"Hemophilia and von Willebrand's Disease: 2. Management," Can Med Assoc J, Jul. 15, 1995, 153(2):147-157.
"Hemostatic Therapy Guideline for Inhibitor-negative Hemophilia Patients," Japanese Journal of Thrombosis and Hemostasis, 2013, 24(6):619-639 (with English translation).
"Hemostatic Therapy Guideline for Inhibitor-positive Hemophilia Patients," Japanese Journal of Thrombosis and Hemostasis, 2013, 24(6):640-658 (with English translation).
ALPROLIX® Intravenous, 2019, 16 pages (with English translation).
Amersdorfer et al., GenPept Accession No. AAC26541, 2001, 8.1.
Asselta et al., "Factor V Deficiency," Semin Thromb Hemost, Jun. 2009, 35(4):382-389.
Astermark et al., "A randomized comparison of bypassing agents in hemophilia complicated by an inhibitor: the FEIBA NovoSeven Comparative (FENOC) Study," Blood, Jan. 15, 2007, 109(2):546-551. Epub Sep. 21, 2006.
Bajaj et al., "A Monoclonal Antibody to Factor IX That Inhibits the Factor VIII:Ca Potentiation of Factor X Activation," J Biol Chem, Sep. 25, 1985, 260(21):11574-11580.
Baker et al., "Immunogenicity of protein therapeutics: The key causes, consequences and challenges," Self/Nonself, Oct. 2010, 1(4):314-322.
Bebbington et al., "High-Level Expression of a Recombinant Antibody From Myeloma Cells Using a Glutamine Synthetase Gene as an Amplifiable Selectable Marker," Biotechnology (NY), Feb. 1992, 10(2):169-175.
Bessos et al., "The Characterization of a Panel of Monoclonal Antibodies to Human Coagulation Factor IX," Thromb Res, Dec. 15, 1985, 40(6):863-867.
Blazar et al., "Infusion of Anti-B7.1 (CD80) and Anti-B7.2 (CD86) Monoclonal Antibodies Inhibits Murine Graft-Versus-Host Disease Lethality In Part Via Direct Effects on CD4$^+$ and CD8$^+$ T Cells," J Immunol, Oct. 15, 1996, 157(8):3250-3259.
Bolton-Maggs et al., "Haemophilias A and B," Lancet, May 24, 2003, 361(9371):1801-1809.
Borrebaeck et al., "Antibody evolution beyond Nature," Nat Biotechnol, Dec. 2002, 20(12):1189-1190.
Bos et al., "Enhanced Transfection of a Bacterial Plasmid into Hybridoma Cells by Electroporation: Application for the Selection of Hybrid Hybridoma (Quadroma) Cell Lines," Hybridoma, Feb. 1992, 11(1):41-51.
Bowen, "Haemophilia A and haemophilia B: molecular insights," Mol Pathol, Feb. 2002, 55(1):1-18.
Brandstetter et al., "X-ray structure of clotting factor IXa: Active site and module structure related to Xase activity and hemophilia B," Proc Natl Acad Sci USA, Oct. 10, 1995, 92(21):9796-9800.

Brennan et al., "Preparation of Bispecific Antibodies by Chemical Recombination of Monoclonal Immunoglobulin G$_1$ Fragments," Science, Jul. 5, 1985, 229(4708):81-83.
Brinkman et al., "Phospholipid-Binding Domain of Factor VIII Is Involved in Endothelial Cell-Mediated Activation of Factor X by Factor IXa," Arterioscler Thromb Vasc Biol, Mar. 1, 2002, 22(3):511-6.
Carter, "Bispecific human IgG by design," J Immunol Methods, Feb. 1, 2001, 248(1-2):7-15.
Cardoso et al., "Neutralizing Human Anti Crotoxin scFv Isolated from a Nonimmunized Phage Library," Scand J Immunol, Apr. 2000, 51(4):337-344.
Chugai Seiyaku Kabushiki Kaisha's letter dated Jun. 12, 2013 regarding oral proceedings scheduled on Jun. 26, 2013, in EP 06730769.4, including Annex A.
Collins et al., "Implications of coagulation factor VIII and IX pharmacokinetics in the prophylactic treatment of haemophilia," Haemophilia, Jan. 2011, 17(1):2-10. doi: 10.1111/j.1365-516.2010.02370.x. Epub Aug. 22, 2010.
Coppola et al., "Acquired Inhibitors of Coagulation Factors: Part I—Acquired Hemophilia A," Semin Thromb Hemost, Jul. 2012, 38(5):433-446. doi: 10.1055/s-0032-1315757. Epub Jun. 27, 2012.
Dahlback, "Blood coagulation," Lancet, May 6, 2000, 355(9215):1627-1632.
Davie, "A Brief Historical Review of the Waterfall/Cascade of Blood Coagulation," J Biol Chem, Dec. 19, 2003, 278(51):50819-50832. Epub Oct. 21, 2003.
Davie et al., "The Coagulation Cascade: Initiation, Maintenance, and Regulation," Biochemistry, Oct. 29, 1991, 30(43):10363-10370.
De Pascalis et al., "Grafting of 'Abbreviated' Complementarity-Determining Regions Containing Specificity-Determining Residues Essential for Ligand Contact to Engineer a Less Immunogenic Humanized Monoclonal Antibody," J Immunol, Sep. 15, 2002, 169(6):3076-3084.
Deng et al., "An Agonist Murine Monoclonal Antibody to the Human c-Mpl Receptor Stimulates Megakaryocytopoiesis," Blood, Sep. 15, 1998, 92(6):1981-1988.
Edelman et al., "The Covalent Structure of an Entire $\gamma$G Immunoglobulin Molecule," Proc Natl Acad Sci USA, May 1969, 63(1):78-85.
Ewert et al., "Stability improvement of antibodies for extracellular and intracellular applications: CDR grafting to stable frameworks and structure-based framework engineering," Methods, Oct. 2004, 34(2):184-199.
Fay, "Activation of factor VIII and mechanisms of cofactor action," Blood Rev, Mar. 2004, 18(1):1-15.
Fay et al., "Nonenzymatic cofactors: factor VIII," Comprehensive Biochemistry, 1986, 13:35-37.
Fay et al., "The size of human factor VIII heterodimers and the effects produced by thrombin," Biochim et Biophys Acta, Jun. 1986, 23:871(3):268-278.
FDA Grants Roche Breakthrough Therapy Designation on Hemophilia Drug, BioPharm International, UBM, Apr. 19, 2018, from http://www.biopharoninternational.conn/fda-grants-roche-breakthrough-therapy-designation-hemophilia-drug.
Figini et al., "In Vitro Assembly of Repertoires of Antibody Chains on the Surface of Phage by Renaturation," J Mol Biol, May 27, 1994, 239(1):68-78.
Franchini et al., "Acquired haemophilia A: A 2013 update," Thromb Haemost, Dec. 2013, 110(6):1114-1120. doi:10.1160/TH13-05-0363. Epub Sep. 5, 2013.
Francois et al., "Construction of a Bispecific Antibody Reacting with the $\alpha$- and $\beta$-Chains of the Human IL-2 Receptor," J Immunol, May 15, 1993, 150(10):4610-4619.
Gelderman et al., "The Inhibitory Effect of CD46, CD55, and CD59 on Complement Activation After Immunotherapeutic Treatment of Cervical Carcinoma Cells with Monoclonal Antibodies or Bispecific Monoclonal Antibodies," Lab Invest, Apr. 2002, 82(4):483-493.
Gonzales et al., "Minimizing the Immunogenicity of Antibodies for Clinical Application," Tumour Biol, Jan.-Feb. 2005, 26(1):31-43.
Griffin et al., "Analysis of heavy and light chain sequences of conventional camelid antibodies from *Camelus dromedarius* and

(56) References Cited

OTHER PUBLICATIONS

*Camelus bactrianus* species," J Immunol Methods, Mar. 2014, 405:35-46. doi: 10.1016/j.jim.2014.01.003. Epub Jan. 18, 2014.

Griffiths et al., "Human anti-self antibodies with high specificity from phage display libraries," EMBO J, Feb. 1993, 12(2):725-734.

Grosse-Hovest et al., "A recombinant bispecific single-chain antibody induces targeted, supra-agonistic CD28-stimulation and tumor cell killing," Eur J Immunol, May 2003, 33(5):1334-1340.

Guidelines for the management of hemophilia, World Federation of Hemophilia, 2005, 52 pages.

Hagiwara et al., "Effect of Emicizumab in improving coagulation ability in the presence of minor amount of Factor IX," Japanese Journal of Thrombosis and Hemostasis, 2017, 28(2):190 (0-012) (with English translation).

Hammerling et al., "Use of Hybrid Antibody With Anti-KG and Anti-Ferritin Specificities in Locating Cell Surface Antigens by Electron Microscopy," J Exp Med, Dec. 1, 1968, 128(6):1461-1473.

Helfrich et al., "A rapid and versatile method for harnessing scFv antibody fragments with various biological effector functions," J Immunol Methods, Apr. 3, 2000, 237(1-2):131-145.

Hoad et al., "Characterisation of monoclonal antibodies to human factor X/Xa Initial observations with a quantitative ELISA procedure," J Immunol Methods, Feb. 15, 1991, 136(2):269-278.

Holliger et al., "'Diabodies': Small bivalent and bispecific antibody fragments," Proc Natl Acad Sci USA, Jul. 15, 1993, 90(14):6444-6448.

Hoyer, "The factor VIII complex: structure and function," Blood, 1981 Jul. 1981, 58(1):1-13.

Hsia et al., "Treatment of acquired factor X inhibitor by plasma exchange with concomitant intravenous immunoglobulin and corticosteroids," Am J Hematol, Apr. 2008, 83(4):318-320.

Hu et al., "Development and Characterization of a Novel Fusion Protein Composed of a Human IgG1 Heavy Chain Constant Region and a Single-Chain Fragment Variable Antibody against Venezuelan Equine Encephalitis Virus," J Biochem, Jan. 2003, 133(1):59-66.

Huse et al., "Generation of a Large Combinatorial Library of the Immunoglobulin Repertoire in Phage Lambda," Science, Dec. 8, 1989, 246(4935):1275-1281.

Igawa, "Next Generation Antibody Therapeutics Using Bispecific Antibody Technology," The Pharmaceutical Society of Japan, Jul. 1, 2017, 137(7):831-836 (with English translation).

Igawa, "Technological Development of Bispecific Antibodies and Creation of Pharmaceuticals," Experimental Medicine, Jul. 1, 2018, 36:1823-1829, fig.3 (with English translation).

Igawa, Chapter 17 "Innovative Technology to develop Bispecific Antibody," CSJ Current Review 30, Part II, Aug. 30, 2018, pp. 157-163, fig. 17-3 (with English translation).

Iwahashi et al., "CDR substitutions of a humanized monoclonal antibody (CC49): contributions of individual CDRs to antigen binding and immunogenicity," Mol Immunol, Oct.-Nov. 1999, 36(15-16):1079-91.

Janeway et al., Chapter 3 "Structure of the Antibody Molecule and Immunoglobulin Genes," Immunobiology, Garland Press, 3$^{rd}$ ed., 1997, pp. 3:1-3:11.

Jirholt et al., "Exploiting sequence space: shuffling in vivo formed complementarity determining regions into a master framework," Gene, Jul. 30, 1998, 215(2):471-476.

Kang et al., "Linkage of recognition and replication functions by assembling combinatorial antibody Fab libraries along phage surfaces," Proc Natl Acad Sci USA, May 15, 1991, 88(10):4363-4366.

Karpovsky et al., "Production of Target-Specific Effector Cells Using Hetero-Cross-Linked Aggregates Containing Anti-Target Cell and Anti-Fcγ Receptor Antibodies," J Exp Med, Dec. 1, 1984, 160(6):1686-1701.

Kerschbaumer et al., "An Antibody Specific for Coagulation Factor IX Enhances the Activity of the Intrinsic Factor X-activating Complex," J Biol Chem, Sep. 24, 2004, 279(39):40445-40450. Epub Jul. 20, 2004.

Kim et al., "Mammalian type I interferon receptors consists of two subunits: IFNaR1 and IFNaR2," Gene, Sep. 1, 1997, 196(1-2):279-286.

Kim et al., "Antibody light chain variable domains and their biophysically improved versions for human immunotherapy," mAbs, Jan.-Feb. 2014, 6(1):219-235. doi: 10.4161/mabs.26844.

Kitazawa et al., "A bispecific antibody to factors IXa and X restores factor VIII hemostatic activity in a hemophilia A model," Nat Med, Sep. 2012, 18(10):1570-1574. doi: 10.1038/nm.2942. Epub Sep. 30, 2012.

Kroesen et al., "Phase I study of intravenously applied bispecific antibody in renal cell cancer patients receiving subcutaneous interleukin 2," Br J Cancer, Oct. 1994, 70(4):652-661.

Kruse-Jarres, "Inhibitors: our greatest challenge. Can we minimize the incidence?," Haemophilia, Jan. 2013, 19(Suppl 1):2-7. doi: 10.1111/hae. 12049.

Kurokawa et al., "Enhanced Fibrinolysis by a Bispecific Monoclonal Antibody Reactive to Fibrin and Tissue Plasminogen Activator," Bio/Technology, Nov. 1989, 7:1163-1167.

Lacroix-Desmazes et al., "Dynamics of factor VIII interactions determine its immunologic fate in hemophilia A," Blood, Jul. 15, 2008, 112(2):240-249. doi: 10.1182/blood-2008-02-124941. Epub May 9, 2008.

Lapan et al., "Interaction of the A1 Subunit of Factor VIIIa and the Serine Protease Domain of Factor X Identified by Zero-length Cross-linking," Thromb Haemost, Sep. 1998, 80(3):418-422.

Le Doussal et al., "Bispecific Monoclonal Antibody-Mediated Targeting of an Indium-111-Labeled DTPA Dimer to Primary Colorectal Tumors: Pharmacokinetics, Biodistribution, Scintigraphy and Immune Response," J Nucl Med, Oct. 1993, 34(10):1662-1671.

Lenting et al., "The Life Cycle of Coagulation Factor VIII in View of Its Structure and Function," Blood, Dec. 1, 1998, 92(11):3983-3996.

Lillicrap, "von Willebrand disease: advances in pathogenetic understanding, diagnosis, and therapy," Blood, Nov. 28, 2013, 122(23):3735-3740. doi: 10.1182/blood-2013-06-498303. Epub Sep. 24, 2013.

Lindsay, Chapter 4 "Determination of the Kinetics and Mechanism of tg-FIX Activation by Factor XIa," 2004, pp. 49-75.

Link et al., "Production and Characterization of a Bispecific IgG Capable of Inducing T-Cell-Mediated Lysis of Malignant B Cells," Blood, Jun. 15, 1993, 81(12):3343-3349.

Lofqvist et al., "Haemophilia prophylaxis in young patients—a long-term follow-up," J Intern Med, May 1997, 241(5):395-400.

Lu et al., "Fab-scFv fusion protein: an efficient approach to production of bispecific antibody fragments," J Immunol Methods, Sep. 15, 2002, 267(2):213-226.

Lu et al., "Di-diabody: a novel tetravalent bispecific antibody molecule by design," J Immunol Methods, Aug. 2003, 279(1-2):219-232.

Maeda et al., Novel Antibody Modification Techniques and their Application to Antibody Therapeutics, Farumashia, 2015, 51:424-428, claim 5 (with English translation).

Massino et al., "Quantitative analysis of the products of IgG chain recombination in hybrid hybridomas based on affinity chromatography and radioimmunoassay," J Immunol Methods, Feb. 14, 1997, 201(1):57-66.

McCafferty et al., "Phage antibodies: filamentous phage displaying antibody variable domains," Nature, Dec. 6, 1990, 348(6301):552-554.

Menegatti et al., "Factor X Deficiency," Semin Thromb Hemost, Jun. 2009, 35(4):407-415.

Merchant et al., "An efficient route to human bispecific IgG," Nat Biotechnol, Jul. 1998, 16(7):677-681.

Mertens et al., "Factor VIII-Factor IX Interactions: Molecular Sites Involved in Enzyme-Cofactor Complex Assembly," Thromb Haemost, Aug. 1999, 82(2):209-217.

Milstein et al., "Hybrid hybridomas and their use in immunohistochemistry," Nature, Oct. 6-12, 1983, 305(5934):537-540.

Minami et al., "Bispecific Antibody ACE910 Improves Coagulation Function in Plasma of Patients with Factor XI Deficiency," Japanese Journal of Thrombosis and Hemostasis, 2015, 26(2):188 (0-024) (with English translation).

(56) References Cited

OTHER PUBLICATIONS

Miyata, "Factor IX Abnormality—Molecular Defects of Factor IX," Japanese Journal of Thrombosis and Hemostasis, 1991, 2(1):1-11 (with English translation).

Miyazaki et al., "Generation of bispecific IgG, which mimics the cofactor function of blood coagulation factor VIII," 2006, (2P-B-161).

Morrison, "Two heads are better than one," Nat Biotechnol, Nov. 2007, 25(11):1233-1234.

Muto et al., "Anti-factor IXa/X bispecific antibody (ACE910): hemostatic potency against ongoing bleeds in a hemophilia A model and the possibility of routine supplementation," J Thromb Haemost, Feb. 2014, 12(2) :206-213. doi: 10.1111/jth.12474.

Muto et al., "Anti-factor IXa/X bispecific antibody ACE910 prevents joint bleeds in a long-term primate model of acquired hemophilia A," Blood, Nov. 13, 2014, 124(20):3165-3171. doi: 10.1182/blood-2014-07-585737. Epub Oct. 1, 2014.

"National Haemophilia Foundation (NHF) Medical and Scientific Advisory Council (MASAC) Recommendations Concerning Prophylaxis," Medical Bulletin, 1994, No. 193, 1 page.

Nilsson et al., "Induction of split tolerance and clinical cure in high-responding hemophiliacs with factor IX antibodies," Proc Natl Acad Sci USA, Dec. 1986, 83(23):9169-9173.

Nilsson et al., "Twenty-five years' experience of prophylactic treatment in severe haemophilia A and B," J Intern Med, Jul. 1992, 232(1):25-32.

Nishimura et al., "Factor IX Fukuoka. Substitution of ASN92 by his in the second epidermal growth factor-like domain results in defective interaction with factors VIIIa/X," J Biol Chem, Nov. 15, 1993, 268(32):24041-24046.

Nitta et al., "Preliminary trial of specific targeting therapy against malignant glioma," Lancet, Feb. 17, 1990, 335(8686):368-371.

Nogami, "Bispecific Antibody that Substitutes for Factor VIII in the Treatment of Childhood Hemophilia A," The Japanese Journal of Pediatric Hematology/Oncology, 2016, 53(2):69-74 (with English translation).

Okubo et al., "The Production and Characterization of Four Monoclonal Antibodies to Human Factor X," J Nara Med Assoc, 1987, 38(1):20-28.

Oldenburg et al., "Emicizumab Prophylaxis in Hemophilia A with Inhibitors," N Engl J Med, Aug. 31, 2017, 377(9):809-818. doi: 10.1056/NEJMoa1703068. Epub Jul. 10, 2017.

Panka et al., "Variable region framework differences result in decreased or increased affinity of variant anti-digoxin antibodies," Proc Natl Acad Sci USA, May 1988, 85(9):3080-3084.

Paul, Chapter 8 "Immunogenicity and Antigen Structure," Fundamental Immunology, Raven Press (NY), $3^{rd}$ ed., 1993, p. 242.

Piper et al., "Interferon Therapy in Primary Care," Prim Care Update Ob Gyns, Jul. 2001, 8(4):163-169.

Portolano et al., "Lack of Promiscuity in Autoantigen-Specific H and L Chain Combinations as Revealed by Human H and L Chain 'Roulette'," J Immunol, Feb. 1, 1993, 150(3):880-887.

Price et al., "Tissue factor and tissue factor pathway inhibitor," Anaesthesia, May 2004, 59(5):483-492.

Ridgway et al., "'Knobs-into-holes' engineering of antibody $C_H3$ domains for heavy chain heterodimerization," Protein Eng, Jul. 1996, 9(7):617-621.

Rudikoff et al., "Single amino acid substitution altering antigen-binding specificity," Proc Natl Acad Sci USA, Mar. 1982, 79(6):1979-1983.

Ruef et al., "A Bispecific Antifibrin-antiplatelet Urokinase Conjugate (BAAUC) Induces Enhanced Clot Lysis and Inhibits Platelet Aggregation," Thromb Haemost, Jul. 1999, 82(1):109-114.

Ruggeri et al., "von Willebrand Factor and von Willebrand Disease," Blood, Oct. 1987, 70(4):895-904.

Saito et al., "Factor VIII Mimetic Antibody: (1) Establishment and Characterization of Anti-factor IX/anti-factor X Bispecific Antibodies," International Society of Thrombosis and Haemostasis, 2005, vol. 3, Issue Supplement s1, p. OR160.

Saito et al., "Establishment of Factor VIII Mimetic Antibodies and Their In Vitro Activities in Hemophilia A," National Hemophilia Foundation Symposia, 2006, 1 page.

Sampei et al., "Identification and multidimensional optimization of an asymmetric bispecific IgG antibody mimicking the function of factor VIII cofactor activity," PLOS One, Feb. 2013, 8(2):e57479, 13 pages. doi: 10.1371/journal.pone.0057479. Epub Feb. 28, 2013.

Sampei et al., "Non-antigen-contacting region of an asymmetric bispecific antibody to factors IXa/X significantly affects factor VIII-mimetic activity," mAbs, Jan. /Feb. 2015, 7(1):120-128. doi: 10.4161/19420862.2015.989028.

Sato et al., "Properties of Two VEGF Receptors, Flt-1 and KDR, in Signal Transduction," Ann NY Acad Sci, May 2000, 902:201-205; discussion 205-207.

Schmidt et al., Chapter 18, Section 18.6, "Hemostasis and Coagulation," Human Physiology, Moscow, 1996, vol. 2, pp. 431-436 (with what are believed to be the corresponding pages from an English version of Human Physiology).

Schmidt et al., Chapter 29 "Enzymes of the pancreatic juice," Human Physiology, Moscow, 1996, vol. 3, pp. 764 (with what are believed to be the corresponding pages from an English version of Human Physiology).

Schmidt et al., Chapter 18, Section 18.6, "Hemostasis and Coagulation," Human Physiology, Springer-Verlag, $2^{nd}$ Completely Revised Edition, 1989, pp. 418-423.

Schmidt et al., Chapter 29 "Enzymes of the pancreatic juice," Human Physiology, Springer-Verlag, $2^{nd}$ Completely Revised Edition, 1989, p. 716.

Schmidt et al., "Structure-Function Relationships in Factor IX and Factor IXa," Trends Cardiovasc Med, Jan. 2003, 13(1):39-45.

Segal et al., "Introduction: bispecific antibodies," J Immunol Methods, Feb. 1, 2001, 248(1-2):1-6.

Shalaby et al., "Development of Humanized Bispecific Antibodies Reactive with Cytotoxic Lymphocytes and Tumor Cells Overexpressing the HER2 Protooncogene," J Exp Med, Jan. 1, 1992, 175(1):217-225.

Shima, "Bispecific antibodies to coagulation factors IXa and X mimic the function of factor VIII," Haemophilia, 2006 World Federation of Haemophilia, 2006, 12 (Suppl. 2), 1 page.

Shima et al., "Factor VIII Mimetic Antibody: (2) In Vitro Assessment of Cofactor Activity in Hemophilia A," Rinsho Ketsueki, Aug. 30, 2005, 46(8):777 (#WS-36-5) (with English translation).

Shima et al., "Factor VIII Mimetic Antibody: (2) In Vitro Assessment of Cofactor Activity in Hemophilia A," International Society of Thrombosis and Haemostasis, 2005, vol. 3, Issue Supplement s1, p. P0038.

Shima et al., "The Forefront and Prospects of Hemophilia Treatment," J Jpn Pediatr Soc, Mar. 1, 2017, 121(3):543-552 (with English translation).

Shima et al., "Factor VIII-Mimetic Function of Humanized Bispecific Antibody in Hemophilia A," N Engl J Med, May 26, 2016, 374(21):2044-2053. doi: 10.1056/NEJMoa1511769.

Shirahata, "5. Future Prospects, 1) Direction for Improvement of Coagulation Factor Preparations," Iyaku (Medicine and Drug) Journal Co., Ltd., Jan. 15, 2009, 280-289 (with English translation).

Singer et al., "Structure of Proteins," Genes & Genomes, Moscow, Mar. 1998, pp. 63-64 (including what are believed to be the corresponding page from an English version of Genes & Genomes).

Soeda et al., "Factor VIII Mimetic Antibody: (1) Establishment of Anti-FIXa/FX Bispecific Antibodies," Rinsho Ketsueki, Aug. 30, 2005, 46(8):728 (#PL-2-4) (with English translation).

Soeda et al., "FVIII-Mimetic Action of Anti-FIXa/Anti-FX Bispecific Antibodies Produced by the Phage Library Method," Jpn J Thromb Hemost, Oct. 1, 2005, 16(5):526 (#O-24) (with English translation).

Stickney et al., "Bifunctional Antibody: A Binary Radiopharmaceutical Delivery System for Imaging Colorectal Carcinoma," Cancer Res, Dec. 15, 1991, 51(24):6650-6655.

Suresh et al., "Advantages of bispecific hybridomas in one-step immunocytochemistry and immunoassays," Methods Enzymol, 1986, 121:210-228.

Suresh et al., "Bispecific Monoclonal Antibodies from Hybrid Hybridomas," Proc Natl Acad Sci USA, Oct. 1986, 83(20):7989-7993.

(56) References Cited

OTHER PUBLICATIONS

Taki, The Journal of Japanese Society on Thrombosis and Hemostasis, Feb. 2, 2002, 13(1):109-113 (with English translation).
Tamura et al., "Structural Correlates of an Anticarcinoma Antibody: Identification of Specificity-Determining Residues (SDRs) and Development of a Minimally Immunogenic Antibody Variant by Retention of SDRs Only," J Immunol, Feb. 1, 2000, 164(3):1432-1441.
Tarantino et al., "Safety of human plasma-derived clotting factor products and their role in haemostasis in patients with haemophilia: meeting report," Haemophilia, Sep. 2007, 13(5):663-669.
Taylor et al., "A new era for hemophilia B treatment," Blood, Apr. 7, 2016, 127(14):1734-1736.
Uchida et al., "A first-in-human phase 1 study of ACE910, a novel factor VIII-mimetic bispecific antibody, in healthy subjects," Blood, Mar. 31, 2016, 127(13):1633-1641. doi: 10.1182/blood-2015-06-650226. Epub Dec. 1, 2015.
Vaughan et al., "Human Antibodies with Sub-nanomolar Affinities Isolated from a Large Non-immunized Phage Display Library," Nat Biotechnol, Mar. 1996, 14(3):309-314.
Vehar et al., "Structure of human factor VIII," Nature, Nov. 22-28, 1984, 312(5992):337-342.
Weiner et al., "A Human Tumor Xenograft Model of Therapy with a Bispecific Monoclonal Antibody Targeting c-erbB-2 and CD16," Cancer Res, Jan. 1, 1993, 53(1):94-100.
Weiner et al., ., "The Role of T Cell Activation in Anti-CD3 x Antitumor Bispecific Antibody Therapy," J Immunol, Mar. 1, 1994, 152(5):2385-2392.
Wood et al., "Expression of active human factor VIII from recombinant DNA clones," Nature, Nov. 22-28, 1984, 312(5992):330-337.
Xiang et al., "Production of Murine V-Human Cr1 Chimeric Anti-Tag72 Antibody Using V Region cDNA Amplified by PCR," Mol Immunol, Aug. 1990, 27(8):809-817.
Yarilin, Fundamentals of Immunology, Moscow, Medicina, 1999, p. 171 (with English translation).
Yoneyama et al., "A Pharmacometric Approach to Substitute for a Conventional Dose-Finding Study in Rare Diseases: Example of Phase III Dose Selection for Emicizumab in Hemophilia A," Clin Pharmacokinet, Sep. 2018, 57(9):1123-1134. doi: 10.1007/s40262-017-0616-3.
Zuo et al., "An efficient route to the production of an IgG-like bispecific antibody," Protein Eng, May 2000, 13(5):361-367.
International Preliminary Report on Patentability for App. Ser. No. PCT/JP2016/088299, dated Jul. 5, 2018, 6 pages.
International Search Report for App. Ser. No. PCT/JP2016/088299, mailed Mar. 28, 2017, 2 pages.
U.S. Appl. No. 18/346,920, filed Jul. 5, 2023, Hattori et al.
U.S. Appl. No. 18/472,949, filed Sep. 22, 2023, Shima et al.
Feng et al., "Factor VIII inhibitors and acquired hemophilia," The 11th National Conference on Thrombosis and Hemostasis, 2007, 5 pages (with English translation).
USPTO Non-Final Office Action in U.S. Appl. No. 16/093,495, dated May 14, 2021, 27 pages.
USPTO Final Office Action in U.S. Appl. No. 16/093,495, dated Nov. 16, 2021, 31 pages.
USPTO Non-Final Office Action in U.S. Appl. No. 16/093,495, dated Apr. 11, 2022, 40 pages.
USPTO Restriction Requirement in U.S. Appl. No. 16/496,089, dated Sep. 1, 2021, 9 pages.
USPTO Non-Final Office Action in U.S. Appl. No. 16/496,089, dated Dec. 21, 2021, 42 pages.
U.S. Appl. No. 17/915,834, filed Sep. 29, 2022, Sato et al.
Colman, "Effects of amino acid sequence changes on antibody-antigen interactions," Res Immunol, Jan. 1994, 145(1):33-36.
Soldatov et al., "Main direction for the development and modification of preparations for the treatment of hemophilia," Hematology and Transfusiology, 61(4):208-215 (with English translation).
U.S. Appl. No. 16/061,429, filed Jun. 12, 2018, Igawa et al.
U.S. Appl. No. 17/389,534, filed Jul. 30, 2021, Hattori et al.
U.S. Appl. No. 17/485,818, filed Sep. 27, 2021, Igawa et al.
U.S. Appl. No. 17/528,371, filed Nov. 17, 2021, Igawa et al.
U.S. Appl. No. 17/699,293, filed Mar. 21, 2022, Hattori et al.
U.S. Appl. No. 17/729,471, filed Apr. 26, 2022, Igawa et al.
Edwards et al., "The Remarkable Flexibility of the Human Antibody Repertoire; Isolation of Over One Thousand Different Antibodies to a Single Protein, BLyS," J Mol Biol, Nov. 14, 2003, 334(1):103-118.
Glatter, "Evaluation of Small-Angle Scattering Data from Lamellar and Cylindrical Particles by the Indirect Transformation Method," J Appl Cryst, 1980, 13:577-584.
Goel et al., "Plasticity within the Antigen-Combining Site May Manifest as Molecular Mimicry in the Humoral Immune Response," J Immunol, Dec. 15, 2004, 173(12):7358-7367.
Grapentin et al., "Protein-Polydimethylsiloxane Particles in Liquid Vial Monoclonal Antibody Formulations Containing Poloxamer 188," J Pharm Sci, Aug. 2020, 109(8):2393-2404.
Janeway et al., "The interaction of the antibody molecule with specific antigen," Immunobiology: The Immune System in Health and Disease, 2001, section 3.6, 5 pages.
Joshi et al., "Avoiding antibody aggregation during processing: establishing hold times," Biotechnol J, Sep. 2014, 9(9):1195-1205. doi: 10.1002/biot.201400052. Epub May 12, 2014.
Kanyavuz et al., "Breaking the law: unconventional strategies for antibody diversification," Nat Rev Immunol, Jun. 2019, 19(6):355-368. doi: 10.1038/S41577-019-0126-7.
Lescar et al., "Crystal Structure of a Cross-reaction Complex between Fab 59.13.7 and Guinea Fowl Lysozyme," Journal of Biological Chemistry, 1995, 270(30):18067-18076.
Lloyd et al., "Modelling the human immune response: performance of a 1011 human antibody repertoire against a broad panel of therapeutically relevant antigens," Protein Eng Des Sel, Mar. 2009, 22(3):159-168. doi: 10.1093/protein/gzn058. Epub Oct. 29, 2008.
Morris, "Epitope Mapping of Protein Antigens by Competition ELISA," The Protein Protocols Handbook, Jan. 1, 1996, pp. 595-600.
Ogiwara et al., "Anti FIXa/FX Bispecific Antibody (Emicizumab) Enhances Plasma Procoagulant Activity in Hemophilia B in the Presence of Very Low Level of Factor IX," Res Pract Thromb Haemost, 2017, 1.suppl 1:749.
Rajagopal et al., "Trehalose Limits Fragment Antibody Aggregation and Influences Charge Variant Formation in Spray-Dried Formulations at Elevated Temperatures," Mol Pharm, Jan. 7, 2019, 16(1):349-358. doi: 10.1021/acs.molpharmaceut.8b01002. Epub Dec. 17, 2018.
Tian et al., "In-depth analysis of subclass-specific conformational preferences of IgG antibodies," IUCrJ, Jan. 1, 2015, 2(Pt 1):9-18. doi: 10.1107/S205225251402209X. eCollection Jan. 1, 2015.
Yada et al., "Spotlight on emicizumab in the management of hemophilia A: patient selection and special considerations," J Blood Med, Jul. 2, 2019, 10:171-181.
USPTO Restriction Requirement in U.S. Appl. No. 16/061,429, dated Jan. 21, 2021, 6 pages.
Fish & Richardson P.C., Reply to Restriction Requirement in U.S. Appl. No. 16/061,429, filed May 10, 2021, 2 pages.
USPTO Non-Final Office Action in U.S. Appl. No. 16/061,429, dated Jun. 30, 2021, 54 pages.
USPTO Restriction Requirement in U.S. Appl. No. 16/459,791, dated Mar. 29, 2021, 7 pages.
U.S. Appl. No. 17/974,914, filed Oct. 27, 2022, Hattori et al.
Yarilin, Fundamentals of Immunology, Moscow, Medicina, 1999, pp. 171-173 (with English translation).
U.S. Appl. No. 18/081,874, filed Dec. 15, 2022, Igawa et al.
Brown et al., "Tolerance to Single, but Not Multiple, Amino Acid Replacements in Antibody $V_H$ CDR2," J Immunol, May 1, 1996, 156(9):3285-3291.
U.S. Appl. No. 18/495,861, filed Oct. 27, 2023, Igawa et al.
Hu et al., "Humanization and characterization of an anti-ricin neutralization monoclonal antibody," PLoS One, Sep. 2012, 7(9):e45595, 9 pages.
Igawa et al., "Generation of a Novel Bispecific Antibody (ACE910) Against Activated Factor IX and Factor X Mimicking the Function of Factor VIII Cofactor Activity," Blood, Nov. 1, 20126, 120(21):1126, 6 pages.
USPTO Final Office Action in U.S. Appl. No. 16/936,575, dated Nov. 7, 2023, 17 pages.

(56) References Cited

OTHER PUBLICATIONS

USPTO Non-Final Office Action in U.S. Appl. No. 16/093,495, dated Aug. 25, 2023, 43 pages.
U.S. Appl. No. 10/575,905, Hattori et al., filed Apr. 30, 2007 (abandoned).
U.S. Appl. No. 11/910,836, Hattori et al., filed Jan. 12, 2009 (abandoned).
U.S. Appl. No. 13/434,643, Hattori et al., filed Mar. 29, 2012 (abandoned).
U.S. Appl. No. 14/921,590, Hattori et al., filed Oct. 23, 2015 (abandoned).
U.S. Appl. No. 15/172,727, Hattori et al., filed Jun. 3, 2016 (abandoned).
U.S. Appl. No. 15/402,580, Hattori et al., filed Jan. 10, 2017 (abandoned).
U.S. Appl. No. 15/701,630, Hattori et al., filed Sep. 12, 2017 (abandoned).
U.S. Appl. No. 15/963,345, Hattori et al., filed Apr. 26, 2018 (abandoned).
U.S. Appl. No. 16/226,798, Hattori et al., filed Dec. 20, 2018 (abandoned).
U.S. Appl. No. 16/536,385, Hattori et al., filed Aug. 9, 2019 (abandoned).
U.S. Appl. No. 16/825,513, Hattori et al., filed Mar. 20, 2020 (abandoned).
U.S. Appl. No. 17/130,736, Hattori et al., filed Dec. 22, 2020 (abandoned).
U.S. Appl. No. 17/389,534, Hattori et al., filed Jul. 30, 2021 (abandoned).
U.S. Appl. No. 17/699,293, Hattori et al., filed Mar. 21, 2022.
U.S. Appl. No. 14/019,117, Igawa et al., filed Sep. 5, 2013 (abandoned).
U.S. Appl. No. 14/019,712, Igawa et al., filed Sep. 6, 2013 (abandoned).
U.S. Appl. No. 15/288,965, Igawa et al., filed Oct. 7, 2016 (abandoned).
U.S. Appl. No. 16/459,791, Igawa et al., filed Jul. 2, 2019 (abandoned).
U.S. Appl. No. 17/485,818, Igawa et al., filed Sep. 27, 2021 (abandoned).
U.S. Appl. No. 17/729,471, Igawa et al., filed Apr. 26, 2022.
U.S. Appl. No. 16/061,429, Igawa et al., filed Jun. 12, 2018 (abandoned).
U.S. Appl. No. 16/093,495, Saeki et al., filed Oct. 12, 2018.
U.S. Appl. No. 16/936,575, Teranishi et al., filed Jul. 23, 2020.
U.S. Appl. No. 16/318,883, Igawa et al., filed Jan. 18, 2019 (abandoned).
U.S. Appl. No. 17/528,371, Igawa et al., filed Nov. 17, 2021.
U.S. Appl. No. 16/496,089, Shima et al., filed Sep. 20, 2019.
U.S. Appl. No. 16/758,128, Hosoguchi et al., filed Apr. 22, 2020.

* cited by examiner

Hinge region sequences of various ACE910 variants introduced with mutations in the hinge region.

| | Antibody name | 3 | 4 | 5 | 6 | 7 | 8 | 9 | 0 | 1 | 2 | 3 | 4 | 5 | 5a | 5b | 5c | 5d | 5e | 5f | 6 | 7 | 8 | 9 | 0 | 1 | 2 | 3 | 4 | 5 | 6 | 7 | 8 | 9 | SEQ ID NO |
|---|---|---|---|---|---|---|---|---|---|---|---|---|---|---|---|---|---|---|---|---|---|---|---|---|---|---|---|---|---|---|---|---|---|---|---|
| | G4T1E356K | K | R | V | E | S | K | Y | G | - | - | - | P | P | - | - | - | - | - | - | C | P | P | C | P | A | P | E | F | R | R | G | P | S | 32 |
| Deletion of the midportion of the hinge region (low flexibility) | T20P | K | R | V | E | S | K | Y | G | - | - | - | P | - | - | - | - | - | - | - | C | P | P | C | P | A | P | E | F | R | R | G | P | S | 33 |
| | T21P | K | R | V | E | S | K | Y | G | - | - | - | - | - | - | - | - | - | - | - | C | P | P | C | P | A | P | E | F | R | R | G | P | S | 34 |
| | T22P | K | R | V | E | S | K | P | - | - | - | - | - | - | - | - | - | - | - | - | C | P | P | C | P | A | P | E | F | R | R | G | P | S | 35 |
| | T23P | K | R | V | E | S | K | P | P | - | - | - | - | - | - | - | - | - | - | - | C | P | P | C | P | A | P | E | F | R | R | G | P | S | 36 |
| | T24P | K | R | V | E | S | K | P | P | P | - | - | - | - | - | - | - | - | - | - | C | P | P | C | P | A | P | E | F | R | R | G | P | S | 37 |
| Modification at the Pro positions (modification of orientation) | T25P | K | R | V | E | S | K | P | P | - | - | - | P | P | - | - | - | - | - | - | C | P | P | C | P | A | P | E | F | R | R | G | P | S | 38 |
| | T26P | K | R | V | E | S | K | G | G | - | - | - | P | P | - | - | - | - | - | - | C | P | P | C | P | A | P | E | F | R | R | G | P | S | 39 |
| | T27P | K | R | V | E | S | K | P | G | - | - | - | P | P | - | - | - | - | - | - | C | P | P | C | P | A | P | E | F | R | R | G | P | S | 40 |
| | T28P | K | R | V | E | S | K | Y | Y | - | - | - | P | P | - | - | - | - | - | - | C | P | P | C | P | A | P | E | F | R | R | G | P | S | 41 |
| | T29P | K | R | V | E | S | K | Y | P | - | - | - | P | P | - | - | - | - | - | - | C | P | P | C | P | A | P | E | F | R | R | G | P | S | 42 |
| | T30P | K | R | V | E | S | K | Y | G | - | - | - | Y | P | - | - | - | - | - | - | C | P | P | C | P | A | P | E | F | R | R | G | P | S | 43 |
| | T31P | K | R | V | E | S | K | Y | G | - | - | - | G | P | - | - | - | - | - | - | C | P | P | C | P | A | P | E | F | R | R | G | P | S | 44 |
| | T32P | K | R | V | E | S | K | Y | G | - | - | - | P | Y | - | - | - | - | - | - | C | P | P | C | P | A | P | E | F | R | R | G | P | S | 45 |
| | T33P | K | R | V | E | S | K | Y | G | - | - | - | P | G | - | - | - | - | - | - | C | P | P | C | P | A | P | E | F | R | R | G | P | S | 46 |
| | T34P | K | R | V | E | S | K | Y | P | - | - | - | G | P | - | - | - | - | - | - | C | P | P | C | P | A | P | E | F | R | R | G | P | S | 47 |
| | T35P | K | R | V | E | S | K | Y | P | - | - | - | P | G | - | - | - | - | - | - | C | P | P | C | P | A | P | E | F | R | R | G | P | S | 48 |
| | T36P | K | R | V | E | S | K | G | Y | - | - | - | P | P | - | - | - | - | - | - | C | P | P | C | P | A | P | E | F | R | R | G | P | S | 49 |
| | T37P | K | R | V | E | S | K | G | P | - | - | - | Y | P | - | - | - | - | - | - | C | P | P | C | P | A | P | E | F | R | R | G | P | S | 50 |
| | T38P | K | R | V | E | S | K | G | P | - | - | - | P | Y | - | - | - | - | - | - | C | P | P | C | P | A | P | E | F | R | R | G | P | S | 51 |
| | T39P | K | R | V | E | S | K | P | Y | - | - | - | G | P | - | - | - | - | - | - | C | P | P | C | P | A | P | E | F | R | R | G | P | S | 52 |
| | T40P | K | R | V | E | S | K | P | Y | - | - | - | P | G | - | - | - | - | - | - | C | P | P | C | P | A | P | E | F | R | R | G | P | S | 53 |
| | T41P | K | R | V | E | S | K | P | G | - | - | - | Y | P | - | - | - | - | - | - | C | P | P | C | P | A | P | E | F | R | R | G | P | S | 54 |
| | T42P | K | R | V | E | S | K | P | G | - | - | - | P | Y | - | - | - | - | - | - | C | P | P | C | P | A | P | E | F | R | R | G | P | S | 55 |
| | T43P | K | R | V | E | S | K | P | P | - | - | - | Y | G | - | - | - | - | - | - | C | P | P | C | P | A | P | E | F | R | R | G | P | S | 56 |
| | T44P | K | R | V | E | S | K | P | P | - | - | - | G | Y | - | - | - | - | - | - | C | P | P | C | P | A | P | E | F | R | R | G | P | S | 57 |
| S-S x 3 | T45P | K | R | V | E | S | K | Y | C | - | - | - | P | P | - | - | - | - | - | - | C | P | P | C | P | A | P | E | F | R | R | G | P | S | 58 |
| AAA (Low flexibility) | T46P | K | R | V | A | A | A | - | - | - | - | - | - | - | - | - | - | - | - | - | C | - | - | - | - | A | P | E | F | R | R | G | P | S | 59 |
| Deletion of the hinge region | T47P | K | R | V | - | - | - | - | - | - | - | - | - | - | - | - | - | - | - | - | - | - | - | - | - | A | P | E | F | R | R | G | P | S | 60 |
| IgA2 | T48P | K | R | V | P | - | - | - | - | - | - | - | - | - | - | - | - | - | - | - | C | P | P | C | P | A | P | E | F | R | R | G | P | S | 61 |
| IgA2 (High flexibility) | T49P | K | R | V | E | S | K | Y | G | - | - | - | P | P | - | - | - | - | - | - | C | P | V | P | P | P | P | P | C | C | H | P | P | S | 62 |
| IgG3 | T50P | K | R | V | E | S | K | S | - | - | C | D | T | P | P | P | C | P | R | C | P | G | P | S | V | A | P | E | F | R | R | G | P | S | 63 |
| Deletion of the IgG1 hinge region (enhancement of agonist activity) | T52P | K | R | V | E | P | K | S | C | - | - | - | D | K | - | - | - | - | - | - | C | P | P | C | P | A | P | E | F | R | R | G | P | S | 64 |
| | T53P | K | R | V | E | P | K | S | C | - | - | - | D | T | H | T | - | - | - | - | C | P | P | C | P | A | P | E | F | R | R | G | P | S | 65 |
| | T54P | K | R | V | E | P | K | S | C | - | - | - | - | T | H | T | - | - | - | - | C | P | P | C | P | A | P | E | F | R | R | G | P | S | 66 |
| | T55P | K | R | V | E | P | C | T | H | - | - | - | T | - | - | - | - | - | - | - | C | P | P | C | P | A | P | E | F | R | R | G | P | S | 67 |
| | T59k | K | R | - | - | - | - | P | P | - | - | - | P | P | - | - | - | - | - | - | C | P | P | C | P | A | P | E | F | R | R | G | P | S | 68 |
| | T67k | K | R | V | A | A | A | - | - | - | - | - | - | - | - | - | - | - | - | - | C | P | P | C | P | A | P | E | F | R | R | G | P | S | 69 |
| | T68k | K | R | V | A | A | - | - | - | - | - | - | - | - | - | - | - | - | - | - | C | - | - | - | - | A | P | E | F | R | R | G | P | S | 70 |
| | T69k | K | R | V | A | A | A | - | - | - | - | - | - | - | - | - | - | - | - | - | C | - | - | - | - | A | P | E | F | R | R | G | P | S | 71 |
| | T70k | K | R | V | P | P | P | - | - | - | - | - | - | - | - | - | - | - | - | - | C | P | P | C | P | A | P | E | F | R | R | G | P | S | 72 |
| | T71k | K | R | V | A | - | - | - | - | - | - | - | - | - | - | - | - | - | - | - | C | P | P | C | P | A | P | E | F | R | R | G | P | S | 73 |
| | T72k | K | R | V | G | G | G | - | - | - | - | - | - | - | - | - | - | - | - | - | C | P | P | C | P | A | P | E | F | R | R | G | P | S | 74 |
| | T73k | K | R | V | G | G | G | - | - | - | - | - | - | - | - | - | - | - | - | - | C | - | - | - | - | A | P | E | F | R | R | G | P | S | 75 |

FIG. 5

BISPECIFIC ANTIBODIES WHICH BIND BLOOD COAGULATION FACTOR VIII AND HAVE ENHANCED ACTIVITY, AND METHODS OF USE THEREOF FOR TREATING BLEEDING AND ASSOCIATED CONDITIONS

CROSS-REFERENCE TO RELATED APPLICATIONS

This application is a divisional of U.S. application Ser. No. 16/061,429, filed on Jun. 12, 2018 (now abandoned), which is the National Stage of International Application No. PCT/JP2016/088299, filed on Dec. 22, 2016, which claims the benefit of Japanese Application No. 2015-253324, filed on Dec. 25, 2015.

SEQUENCE LISTING

This application contains a Sequence Listing that has been submitted electronically as an ASCII text file named SequenceListing.txt. The ASCII text file, created on Dec. 14, 2021, is 110 kilobytes in size. The material in the ASCII text file is hereby incorporated by reference in its entirety.

TECHNICAL FIELD

The present invention relates to antibodies having enhanced activity, pharmaceutical compositions comprising such antibodies as active ingredients, methods for producing them, and methods for enhancing antibody activity. More specifically, the present invention relates to bispecific antibodies having blood coagulation factor VIII (FVIII) mimetic activity higher than that of ACE910.

BACKGROUND ART

Antibodies are drawing attention as pharmaceuticals as they are highly stable in plasma and have few adverse effects. Of them, a number of IgG-type antibody pharmaceuticals are available on the market and many antibody pharmaceuticals are currently under development (Non-patent Documents 1, 2 and 3).

Hemophilia A is a bleeding abnormality caused by a hereditary decrease or deficiency of FVIII function. Hemophilia A patients are generally administered with an FVIII formulation for bleeding (on-demand administration). In recent years, FVIII formulations are also administered prophylactically to prevent bleeding events (preventive administration; Non-patent Documents 1 and 2). The half-life of FVIII formulations in blood is approximately 12 to 16 hours. Therefore, for continuous prevention, FVIII formulations are administered to patients three times a week (Non-patent Documents 3 and 4). In on-demand administration, FVIII formulations are also additionally administered as necessary at an interval to prevent rebleeding. In addition, the administration of FVIII formulations is intravenous. Therefore, there has been a strong need for pharmaceutical agents with a lesser burden in administration than FVIII formulations.

Occasionally, antibodies against FVIII (inhibitors) are raised in hemophilia patients. Such inhibitors counteract the effects of the FVIII formulations. For bleeding in patients who have developed inhibitors (inhibitor patients), bypassing agents are administered. Their mechanisms of action do not depend on the FVIII function, that is, the function of catalyzing the activation of blood coagulation factor X (FX) by activated blood coagulation factor IX (FIXa). Therefore, in some cases, bypassing agents cannot sufficiently stop the bleeding. Accordingly, there has been a strong need for pharmaceutical agents that are not affected by the presence of inhibitors and which functionally substitute for FVIII.

As a means for solving the problem, bispecific antibodies that functionally substitute for FVIII and their use have been reported (Patent Documents 1, 2, 3, and 4). The bispecific antibodies against FIXa and FX can functionally substitute for FVIII by positioning the two factors close to each other to exhibit FVIII mimetic activity (Non-patent Document 5). It has been reported that the FVIII mimetic activity of the antibodies can be enhanced by optimizing the affinity towards FIXa and FX (Non-patent Document 6). Furthermore, the FVIII mimetic activity of the antibodies is known to be affected by the IgG isotype, disulfide bond pattern, amino acid sequence of the hinge region, and the presence or absence of sugar chains in the Fc region (Non-patent Document 7). ACE910 having high FVIII mimetic activity, which is one of these antibodies, has been reported to exhibit hemostatic effects in monkey models of hemophilia (Non-patent Documents 8 and 9). However, there has been no report on a bispecific antibody having FVIII mimetic activity higher than that of ACE910.

CITATION LIST

Patent Documents

[Patent Document 1] WO 2005/035754
[Patent Document 2] WO 2005/035756
[Patent Document 3] WO 2006/109592
[Patent Document 4] WO 2012/067176

Non-Patent Documents

[Non-patent Document 1] Blood 58, 1-13 (1981).
[Non-patent Document 2] Nature 312, 330-337 (1984).
[Non-patent Document 3] Nature 312, 337-342 (1984).
[Non-patent Document 4] Biochim. Biophys. Acta 871, 268-278 (1986).
[Non-patent Document 5] Nat Med. 2012 October; 18(10):1570-4.
[Non-patent Document 6] PLoS One. 2013; 8(2):e57479.
[Non-patent Document 7] MAbs. 2015; 7(1):120-8.
[Non-patent Document 8] J Thromb Haemost. 2014 February; 12(2):206-213.
[Non-patent Document 9] Blood. 2014 Nov. 13; 124(20): 3165-71.

SUMMARY OF THE INVENTION

Problems to be Solved by the Invention

The present invention was achieved in view of the above circumstances. An objective of the present invention is to provide antibodies having enhanced activity, pharmaceutical compositions containing such antibodies as active ingredients, methods for producing them, methods for enhancing antibody activity, and such. More specifically, an objective of the present invention is to provide mutations in the constant region sites for preparing bispecific antibodies having FVIII mimetic activity higher than that of ACE910, and FIXa/FX bispecific antibodies having such mutations, pharmaceutical compositions containing the antibodies as active ingredients, or methods for treating hemophilia A using the pharmaceutical compositions.

Means for Solving the Problems

To solve the above-mentioned problems, the present inventors produced ACE910 variants in which various sites of the constant regions were modified, and succeeded in discovering bispecific antibodies having FVIII mimetic activity higher than that of ACE910. The inventors also succeeded in identifying mutations that elevate the FVIII mimetic activity and discovering methods for elevating the FVIII mimetic activity by using the mutations. The present invention is based on such findings and relates to the following:

[1] A modified bispecific antibody against blood coagulation factor IX and/or activated blood coagulation factor IX and blood coagulation factor X, wherein the antibody comprises a modification of at least one amino acid residue in the constant region of the antibody, and wherein the antibody has higher blood coagulation factor VIII mimetic activity than that of a bispecific antibody, which is an antibody before the modification, in which an H chain comprising the amino acid sequence of SEQ ID NO: 1 associates with an L chain comprising the amino acid sequence of SEQ ID NO: 3, and an H chain comprising the amino acid sequence of SEQ ID NO: 2 associates with an L chain comprising the amino acid sequence of SEQ ID NO: 3;

[2] The antibody of [1], wherein the modification is a modification in a CH3 region and/or hinge region;

[3] The antibody of [2], wherein the modification in the CH3 region is a modification at position 434 according to EU numbering;

[4] The antibody of [3], wherein the modification at position 434 according to EU numbering is a modification to Tyr (Y);

[5] The antibody of [2], wherein the modification in the hinge region is a modification of positions 216 to 230 according to EU numbering to AAAC;

[6] A pharmaceutical composition comprising the antibody of any one of [1] to [5], and a pharmaceutically acceptable carrier;

[7] The composition of [6], which is a pharmaceutical composition for use in prevention and/or treatment of bleeding, a disease accompanying bleeding, or a disease caused by bleeding, wherein the disease is a disease that develops and/or progresses by a decrease or deficiency in the activity of blood coagulation factor VIII and/or activated blood coagulation factor VIII;

[8] The composition of [7], wherein the disease that develops and/or progresses by a decrease or deficiency in the activity of blood coagulation factor VIII and/or activated blood coagulation factor VIII is hemophilia A, acquired hemophilia, von Willebrand's disease, or a disease in which an inhibitor against blood coagulation factor VIII and/or activated blood coagulation factor VII has been raised;

[9] A kit for use in a method for prevention and/or treatment of bleeding, a disease accompanying bleeding, or a disease caused by bleeding, wherein the kit comprises at least the bispecific antibody of any one of [1] to [5];

[10] A method for enhancing the blood coagulation factor VIII mimetic activity of a bispecific antibody against blood coagulation factor IX and/or activated blood coagulation factor IX and blood coagulation factor X, wherein the method modifies at least one amino acid residue in the constant region of a bispecific antibody in which an H chain comprising the amino acid sequence of SEQ ID NO: 1 associates with an L chain comprising the amino acid sequence of SEQ ID NO: 3, and an H chain comprising the amino acid sequence of SEQ ID NO: 2 associates with an L chain comprising the amino acid sequence of SEQ ID NO: 3;

[11] The method of [10], wherein the modification is a modification of at least one amino acid residue in a CH3 region and/or hinge region;

[12] The method of [11], wherein the modification in the CH3 region is a modification at position 434 according to EU numbering;

[13] The method of [12], wherein the modification at position 434 is a modification to Tyr (Y);

[14] The method of [11], wherein the modification in the hinge region is a modification of positions 216 to 230 according to EU numbering to AAAC;

[15] A method for producing a bispecific antibody against blood coagulation factor IX and/or activated blood coagulation factor IX and blood coagulation factor X, wherein the method comprises: (a) modifying at least one amino acid residue in the constant region of a bispecific antibody in which an H chain comprising the amino acid sequence of SEQ ID NO: 1 associates with an L chain comprising the amino acid sequence of SEQ ID NO: 3, and an H chain comprising the amino acid sequence of SEQ ID NO: 2 associates with an L chain comprising the amino acid sequence of SEQ ID NO: 3, which is an antibody before the modification, so that the blood coagulation factor VIII mimetic activity is enhanced compared to the antibody before the modification, by modifying a nucleic acid encoding an antibody comprising said amino acid residue; (b) culturing a host cell to express the nucleic acid; and (c) collecting the antibody from a culture of the host cell;

[16] a method for prevention and/or treatment of bleeding, a disease accompanying bleeding, or a disease caused by bleeding, which comprises the step of administering the antibody of any one of [1] to [5];

[17] the antibody of any one of [1] to [5], for use in prevention and/or treatment of bleeding, a disease accompanying bleeding, or a disease caused by bleeding;

[18] use of the antibody of any one of [1] to [5] in the manufacture of a prophylactic agent and/or a therapeutic agent for bleeding, a disease accompanying bleeding, or a disease caused by bleeding; and

[19] the method of [16] or the antibody for use of [17], or the use of [18], wherein the disease is a disease that develops and/or progresses by a decrease or deficiency in the activity of blood coagulation factor VIII and/or activated blood coagulation factor VIII, or preferably hemophilia A, acquired hemophilia, von Willebrand's disease, or a disease in which an inhibitor against blood coagulation factor VIII and/or activated blood coagulation factor VIII has been raised.

Effects of the Invention

The present invention provides bispecific antibodies having FVIII mimetic activity higher than that of ACE910. Furthermore, the present invention provides mutations that elevate the FVIII mimetic activity, and methods for elevating the FVIII mimetic activity that use the mutations.

BRIEF DESCRIPTION OF THE DRAWINGS

FIG. 5 shows mutated hinge region sequences of some ACE910 variants.

MODE FOR CARRYING OUT THE INVENTION

Figure 1:
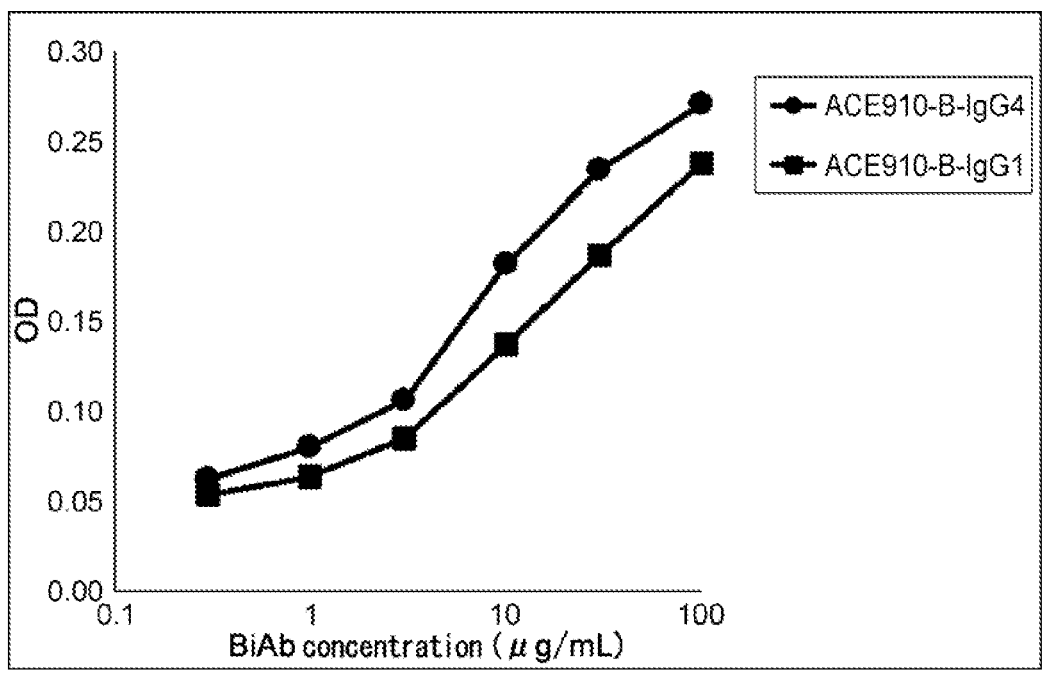
FIG. 1 shows the effects of human IgG1 and human IgG4 isotypes on the FVIII mimetic activity of ACE910.

An embodiment of the present invention relates to an antibody comprising a modified constant region, which comprises a mutation of at least one amino acid residue in the constant region, and has higher activity than that of the antibody before the modification.

The "antibody comprising a constant region" in the present invention is not particularly limited as long as it is an antibody that contains a constant region, and it may be an IgG-type or bispecific antibody.

In one embodiment of the present invention, constant regions are preferably antibody constant regions, more preferably IgG1, IgG2, IgG3, and IgG4-type antibody constant regions, and even more preferably human IgG1, IgG2, IgG3, and IgG4-type antibody constant regions. Furthermore, in another embodiment of the present invention, constant regions are preferably heavy chain constant regions, more preferably IgG1, IgG2, IgG3, and IgG4-type heavy chain constant regions, and even more preferably human IgG1, IgG2, IgG3, and IgG4-type heavy chain constant regions. The amino acid sequences of the human IgG1 constant region, the human IgG2 constant region, the human IgG3 constant region, and the human IgG4 constant region are known. For the constant regions of human IgG1, human IgG2, human IgG3, and human IgG4, a plurality of allotype sequences with genetic polymorphism are described in Sequences of proteins of immunological interest, NIH Publication No. 91-3242, and any of them can be used in the present invention. Amino acid-modified constant regions of the present invention may contain other amino acid mutations or modifications, as long as they include an amino acid mutation of the present invention.

An Fc region contains the amino acid sequence derived from the heavy chain constant region of an antibody. The Fc region is a portion of the heavy chain constant region of an antibody, starting from the N terminal end of the hinge region, which corresponds to the papain cleavage site at an amino acid around position 216 according to EU numbering, and contains the hinge, CH2, and CH3 domains.

The term "hinge region" denotes an antibody heavy chain polypeptide portion in a wild-type antibody heavy chain that joins the CH1 domain and the CH2 domain, e.g., from about position 216 to about position 230 according to the EU numbering system by Kabat, or from about position 226 to about position 230 according to the EU numbering system by Kabat. The hinge regions of other IgG subclasses can be determined by alignment with the hinge region cysteine residues of the IgG1 subclass sequence.

In the present invention, "polypeptide" normally refers to a protein and peptide having a length of approximately ten amino acids or longer. Ordinarily, the polypeptides are organism-derived polypeptides, but are not particularly limited thereto, and may be, for example, polypeptides comprising an artificially designed sequence. Furthermore, they may be any native polypeptides, or synthetic polypeptides, recombinant polypeptides, or such. Additionally, fragments of the above-mentioned polypeptide are also included in the polypeptides of the present invention.

EU Numbering and Kabat Numbering

According to the methods used in the present invention, amino acid positions assigned to antibody CDR and FR are specified according to Kabat's numbering (Sequences of Proteins of Immunological Interest (National Institute of Health, Bethesda, Md., 1987 and 1991)). Herein, when an antigen-binding molecule is an antibody or antigen-binding fragment, variable region amino acids are indicated by Kabat numbering, while constant region amino acids are indicated by EU numbering based on Kabat's amino acid positions.

In one embodiment of the present invention, "modification of amino acid residue" is not particularly limited as long as it is a modification that enhances activity compared to that of the antibody before the modification, and it is preferably a modification in the CH3 region or the hinge region. Particularly preferably, it is a modification at position 434 according to EU numbering, and more preferably, it is a modification that replaces Asn (N) at position 434 according to EU numbering with Tyr (Y). Particularly preferably, it is a modification in the hinge region, and more preferably it is a modification of positions 216 to 230 according to EU numbering to AAAC. Furthermore, the present invention includes a modification of positions 216 to 230 according to EU numbering to AAAC by partially modifying positions 216 to 230 according to EU numbering. As long as the mutation mentioned above is included, other mutations may also be included.

In one embodiment of the present invention, "modification" or "modify" refers to substitution of the original amino acid residue with another amino acid residue, deletion of the original amino acid residue, addition of a new amino acid residue, and combinations thereof. Furthermore, "mutation" refers to substitution of the original amino acid residue with another amino acid residue, deletion of the original amino acid residue, addition of a new amino acid residue, and combinations thereof. Herein, the terms "modification" and "mutation" are used synonymously.

In one embodiment of the present invention, "activity" refers to, for example, the binding ability of the antibody to an antigen, a biological effect produced by binding of the antibody to an antigen, and such, but is not limited thereto. When the antibody is a bispecific antibody against blood coagulation factor IX (FIX) and/or activated blood coagulation factor IX (FIXa) and blood coagulation factor X (FX), the activity is, for example, blood coagulation factor FVIII (FVIII) mimetic activity.

For example, in the case of FVIII mimetic activity of the above-mentioned bispecific antibody, "having higher activity than that of the antibody before the modification" refers to the fact that the FVIII mimetic activity of the bispecific antibody after the modification is higher than the FVIII mimetic activity of the bispecific antibody before the modification.

FVIII

FVIII is one of a series of molecules involved in blood coagulation. FVIII exhibits cofactor activity when it is activated by thrombin or FXa and promotes the FX activation reaction by FIXa.

FVIII Mimetic Activity

In the present invention, "FVIII mimetic activity" can be rephrased as "FVIII function substituting activity", "activity of functionally substituting for FVIII", "FXa generation promoting activity", and "activity of promoting generation of FXa". In the present invention, the phrases "FVIII function substituting" and "functionally substituting for FVIII" means that FX activation by FIXa is promoted (FXa generation by FIXa is promoted). More specifically, in the present invention, the phrase "functionally substituting for FVIII" means recognizing FIX and/or FIXa, and FX, and promoting activation of FX by FIXa (promoting FXa generation by FIXa). The activity of promoting FXa generation can be evaluated using, for example, a measurement system comprising FIXa, FX, synthetic substrate S-2222 (synthetic substrate of FXa), and phospholipids. Such a measurement system shows correlation with the disease severity and clinical symptoms in hemophilia A cases (Rosen S, Andersson M, Blombdck M et al. Clinical applications of a chromogenic substrate method for determination of FVIII activity. Thromb Haemost 1985; 54: 811-23).

In one embodiment of the present invention, the antibody is not particularly limited but is preferably, for example, a bispecific antibody against FIX and/or FIXa and FX, which has activity of functionally substituting for FVIII. Such an antibody can be obtained according to the methods described, for example, in WO2005/035756, WO2006/109592, and WO2012/067176. Antibodies of the present invention include antibodies described in these documents.

A preferred bispecific antibody includes, for example, ACE910 (emicizumab) (Q499-z121/J327-z119/L404-k) (a bispecific antibody in which the H chain comprising the amino acid sequence of SEQ ID NO: 1 (Q chain) associates with the L chain comprising the amino acid sequence of SEQ ID NO: 3, and the H chain comprising the amino acid sequence of SEQ ID NO: 2 (J chain) associates with the L chain comprising the amino acid sequence of SEQ ID NO: 3), which is a bispecific antibody described in the patent document WO2012/067176. The L chain of this antibody is a so-called common L chain. Herein, ACE910 is also referred to as ACE910-A.

An embodiment of the present invention is a modified bispecific antibody against FIX and/or FIXa and FX, which comprises a modification of at least one amino acid residue, and has higher FVIII mimetic activity than the bispecific antibody, which is the antibody before the modification, in which an H chain comprising the amino acid sequence of SEQ ID NO: 1 associates with an L chain comprising the amino acid sequence of SEQ ID NO: 3, and an H chain comprising the amino acid sequence of SEQ ID NO: 2 associates with an L chain comprising the amino acid sequence of SEQ ID NO: 3.

A specific embodiment of the present invention is a bispecific antibody against FIX and/or FIXa and FX, in which an H chain comprising the amino acid sequence of SEQ ID NO: 1 associates with an L chain comprising the amino acid sequence of SEQ ID NO: 3, and an H chain comprising the amino acid sequence of SEQ ID NO: 2 associates with an L chain comprising the amino acid sequence of SEQ ID NO: 3, which is an antibody whose position 434 according to EU numbering is Tyr (Y).

Another specific embodiment of the present invention is a bispecific antibody against FIX and/or FIXa and FX, in which an H chain comprising the amino acid sequence of SEQ ID NO: 1 associates with an L chain comprising the amino acid sequence of SEQ ID NO: 3, and an H chain comprising the amino acid sequence of SEQ ID NO: 2 associates with an L chain comprising the amino acid sequence of SEQ ID NO: 3, which is an antibody whose positions 216 to 230 according to EU numbering are AAAC.

The term "antibody" is used in the broadest sense, and may be a monoclonal antibody, polyclonal antibody, dimer, multimer, multispecific antibody (for example, bispecific antibody), antibody derivative, and modified antibody product (Miller K et al. J Immunol. 2003, 170(9), 4854-61) as long as it show a desired activity. The antibodies may be mouse antibodies, human antibodies, humanized antibodies, chimeric antibodies, or those derived from other species, or they may be artificially synthesized antibodies. The antibodies disclosed herein can be of any type (for example, IgG, IgE, IgM, IgD, and IgA), class (for example, IgG1, IgG2, IgG3, IgG4, IgA1 and IgA2) or subclass of immunoglobulin. The immunoglobulin can be derived from any species (for example, human, mouse, or rabbit). The terms "antibody", "immune globulin" and "immunoglobulin" are used interchangeably in a broad sense.

The term "antibody derivative" includes a portion of an antibody, preferably a variable region of an antibody, or at least an antigen-binding region of an antibody. Antibody derivatives include, for example, Fab, Fab', F(ab')2, Fv fragments, linear antibodies, and single-chain antibodies (scFv), sc(Fv)$_2$, Fab$_3$, domain antibodies (dAb) (WO2004/058821, WO2003/002609), diabodies, triabodies, tetrabodies, minibodies, and multispecific antibodies formed from antibody derivatives, but are not limited thereto. Here, "Fab" is composed of a single light chain and the CH1 domain and variable region of a single heavy chain. Furthermore, "Fv" is the smallest antibody derivative, and includes a complete antigen-recognizing region and an antigen-binding region. Furthermore, the antibody derivative may be, for example, a fusion with an Fc of an IgG antibody. For example, one can refer to Example 2 in U.S. Pat. No. 5,641,870, specification; Zapata G et al. Protein Eng. 1995, 8(10), 1057-1062; Olafsen T et al. Protein Eng. Design & Sel. 2004, 17(4): 315-323; Holliger P et al. Nat. Biotechnol. 2005, 23(9): 1126-36; Fischer N et al. Pathobiology. 2007, 74(1): 3-14; Shen J et al. J Immunol Methods. 2007, 318, 65-74; and Wu et al. Nat Biotechnol. 2007, 25(11), 1290-7.

Examples of modified antibody products may include antibodies linked to various molecules such as polyethylene glycol (PEG). Antibodies of the present invention include such modified antibody products. The substance to be linked is not limited in the modified antibody products of the present invention. To yield such modified antibody products, chemical modifications can be made to the obtained antibodies. Such methods have already been established in this field.

"Bispecific" antibodies refer to antibodies having variable regions that recognize different epitopes within the same antibody molecule. Bispecific antibodies may be antibodies that recognize two or more different antigens, or antibodies that recognize two or more different epitopes on the same antigen. Bispecific antibodies may include not only whole antibodies but antibody derivatives. Antibodies of the present invention also include bispecific antibodies. Herein, "anti-FIXa/FX bispecific antibody" and "bispecific antibody that binds to FIXa and FX" are used synonymously.

Methods for Producing Genetically Engineered Antibodies

Recombinant antibodies produced by using genetic engineering techniques can be used as the antibodies. Recombinant antibodies can be obtained by cloning DNAs encoding the antibodies from hybridomas or antibody-producing cells such as sensitized lymphocytes that produce antibodies, inserting them into vectors, and then introducing them into hosts (host cells) to produce the antibodies.

The antibodies include human antibodies, mouse antibodies, and rat antibodies, and their origin is not limited. They may also be genetically modified antibodies such as chimeric antibodies and humanized antibodies.

Methods for obtaining human antibodies have already been known. For example, transgenic animals carrying the entire repertoire of human antibody genes can be immunized with antigens of interest to obtain human antibodies of interest (see International Publication WO 93/12227, WO 92/03918, WO 94/02602, WO 94/25585, WO 96/34096, and WO 96/33735).

Genetically modified antibodies can be produced using known methods. Specifically, for example, chimeric antibodies comprise H-chain and L-chain variable regions of an antibody from an immunized animal, and H-chain and L-chain constant regions of a human antibody. Chimeric antibodies can be obtained by linking DNAs encoding the variable regions of the antibody derived from the immunized animal, with DNAs encoding the constant regions of the human antibody, inserting this into an expression vector, and then introducing it into a host to produce the antibodies.

Humanized antibodies are modified antibodies that are also referred to as reshaped human antibodies. A humanized antibody is constructed by transferring the CDRs of an antibody derived from an immunized animal to the complementarity determining regions of a human antibody. Conventional genetic recombination techniques for this are known (see European Patent Application Publication No. EP 239400; International Publication No. WO 96/02576; Sato K et al., Cancer Research 1993, 53: 851-856; and International Publication No. WO 99/51743).

Bispecific antibodies are antibodies that have specificity to two different antigens.

While bispecific antibodies are not limited to those of the IgG type, for example, IgG-type bispecific antibodies can be secreted from a hybrid hybridoma (quadroma) produced by fusing two types of hybridomas that produce IgG antibodies (Milstein C. et al., Nature 1983, 305: 537-540). They can also be secreted by introducing a total of four types of genes including the L-chain and H-chain genes constituting the two types of IgGs of interest into cells to co-express the genes.

In this case, by introducing suitable amino acid substitutions into the CH3 regions of the H chains, IgGs having a heterogeneous combination of H chains can be preferentially secreted (Ridgway J B et al. Protein Engineering 1996, 9: 617-621; Merchant A M et al. Nature Biotechnology 1998, 16: 677-681; WO 2006/106905; Davis J H et al. Protein Eng Des Sel. 2010, 4: 195-202).

Regarding the L chains, since the diversity of L chain variable regions is lower than that of H chain variable regions, one can expect to obtain a common L chain that can confer binding ability to both H chains, and the antibodies of the present invention may be antibodies comprising the common L chain. Bispecific IgGs can be efficiently expressed by introducing the genes of the common L chain and both H chains into cells.

Antibody Production Methods

Antibodies of the present invention can be produced by methods known to those skilled in the art. Specifically, a DNA encoding the antibody of interest is inserted into an expression vector. The insertion into the expression vector is carried out such that the expression will take place under the control of expression regulatory regions such as enhancers and promoters. Next, host cells are transformed using this expression vector to express the antibody. Appropriate combinations of the host and expression vector can be used in this step.

Expression vectors are particularly useful when using the vectors for the purpose of producing the antibody. For example, when the host is Escherichia coli such as JM109, DH5α, HB101, or XL1-Blue, the expression vectors indispensably have a promoter that permits efficient expression in E. coli, for example, lacZ promoter.

The vectors may contain a signal sequence for polypeptide secretion.

The vectors can be transferred to host cells using, for example, calcium chloride methods or electroporation methods.

In addition to the E. coli expression vectors, examples of the vectors for producing the antibody of the present invention include mammal-derived expression vectors (e.g., pcDNA3 (manufactured by Invitrogen Corp.), pEGF-BOS (Nucleic Acids. Res. 1990, 18(17), p5322), pEF, and pCDM8), and insect cell-derived expression vectors (e.g., "Bac-to-BAC baculovirus expression system" (manufactured by GIBCO BRL), and pBacPAK8).

For the purpose of expression in animal cells such as CHO cells, COS cells, or NIH3T3 cells, the vectors indispensably have a promoter necessary for intracellular expression, for example, SV40 promoter (Mulligan et al., Nature (1979) 277, 108), and, more preferably, have a gene for selecting transformed cells. Examples of the genes for selecting transformed cells include drug resistance genes that can be distinguished by drugs (neomycin, G418, and such).

An exemplary method intended to stably express the gene and increase the number of intracellular gene copies is a method of transfecting CHO cells deficient in nucleic acid synthesis pathway with a vector having a DHFR gene for complementation (e.g., pCHOI) and using methotrexate (MTX) to amplify the gene. Furthermore, an exemplary method intended to transiently express the gene is a method of using COS cells having a gene which expresses an SV40 T antigen on the chromosome to transform the cells with a vector having a replication origin of SV40 (pcD, etc.).

The antibodies of the present invention obtained by the methods described above can be isolated from the inside of host cells or the outside of the cells (medium, etc.), and purified to be substantially pure, homogeneous antibodies. The antibodies can be separated and purified by methods ordinarily used for separation or purification for antibody purification, and they are not limited. For example, the antibodies can be separated and purified by appropriately selecting and combining column chromatography, filtration, ultrafiltration, salting-out, solvent precipitation, solvent extraction, distillation, immunoprecipitation, SDS-polyacrylamide gel electrophoresis, isoelectric focusing, dialysis, recrystallization, and such.

The chromatography includes, for example, affinity chromatography, ion exchange chromatography, hydrophobic chromatography, gel filtration, reverse phase chromatography, and adsorption chromatography (Strategies for Protein Purification and Characterization: A Laboratory Course Manual. Ed Daniel R. Marshak et al., Cold Spring Harbor Laboratory Press, 1996). These chromatographic methods can be conducted using liquid chromatography, for example, HPLC and 30 FPLC. Columns used for affinity chromatography include Protein A columns and Protein G columns. Columns using Protein A include, for example, Hyper D®, POROS™, and Sepharose™ FF Protein A columns (GE Amersham Biosciences). The present invention includes antibodies that are highly purified using these purification methods.

The obtained antibodies can be purified to be homogeneous. Antibody separation and purification can be performed using separation and purification methods generally used for proteins. For example, without limitation, the antibodies can be separated and purified by appropriately selecting and combining column chromatography such as affinity chromatography, filtration, ultrafiltration, salting-out, dialysis, SDS-polyacrylamide gel electrophoresis, isoelectric focusing, and such (Antibodies: A Laboratory Manual. Ed Harlow and David Lane, Cold Spring Harbor Laboratory, 1988). Columns used for affinity chromatography include, for example, Protein A columns and Protein G columns.

The present invention provides a pharmaceutical composition comprising an antibody of the present invention and a pharmaceutically acceptable carrier. For example, when the antibody of the present invention is a bispecific antibody against FIX and/or FIXa and FX which has FVIII mimetic activity, the composition is expected to be, for example, a pharmaceutical (pharmaceutical composition) or a pharmaceutical agent for prevention and/or treatment of bleeding, a disease accompanying bleeding, or a disease caused by bleeding.

In the present invention, bleeding, a disease accompanying bleeding, or a disease caused by bleeding is preferably a disease that develops and/or progresses by a decrease or deficiency in the activity of FVIII and/or FVIIIa. Examples of such diseases include, but are not particularly limited to, hemophilia A, a disease in which an inhibitor against FVIII/FVIIIa has been raised, acquired hemophilia, or von Willebrand's disease mentioned above.

Another embodiment of the present invention is a kit for use in a method for prevention and/or treatment of the above-mentioned diseases, which comprises at least an antibody or a composition of the present invention. The kit may include in its package a syringe, injection needle, pharmaceutically acceptable medium, alcohol-soaked cotton, adhesive bandage, instructions describing the method of use, and the like.

Another embodiment of the present invention relates to use of an antibody or a composition of the present invention in the manufacture of prophylactic and/or therapeutic agents for bleeding, a disease accompanying bleeding, or a disease caused by bleeding.

Another embodiment of the present invention relates to a method for prevention and/or treatment of bleeding, a disease accompanying bleeding, or a disease caused by bleeding, which comprises the step of administering an antibody or a composition of the present invention.

Another embodiment of the present invention relates to an antibody or a composition of the present invention for use in prevention and/or treatment of bleeding, a disease accompanying bleeding, or a disease caused by bleeding.

Pharmaceutical compositions used for therapeutic or preventive purposes, which comprise antibodies of the present invention as active ingredients, can be formulated, as necessary, by mixing, with suitable pharmaceutically acceptable carriers, vehicles, and such that are inactive towards the antibodies. For example, sterilized water, physiological saline, stabilizers, excipients, antioxidants (such as ascorbic acid), buffers (such as phosphate, citrate, histidine, and other organic acids), antiseptics, surfactants (such as PEG and Tween® nonionic detergent), chelating agents (such as EDTA), and binders may be used. They may also comprise other low-molecular-weight polypeptides, proteins such as serum albumin, gelatin, and immunoglobulins, amino acids such as glycine, glutamine, asparagine, glutamic acid, aspartic acid, methionine, arginine, and lysine, sugars and carbohydrates such as polysaccharides and monosaccharides, and sugar alcohols such as mannitol and sorbitol. When preparing an aqueous solution for injection, physiological saline and isotonic solutions comprising glucose and other adjuvants such as D-sorbitol, D-mannose, D-mannitol, and sodium chloride may be used, and they may be used in combination with appropriate solubilizers such as alcohol (for example, ethanol), polyalcohols (such as propylene glycol and PEG), and nonionic surfactants (such as polysorbate 80, polysorbate 20, poloxamer 188, and HCO-50). By mixing hyaluronidase into the formulation, a larger fluid volume can be administered subcutaneously (Expert Opin Drug Deliv. 2007 July; 4(4): 427-40).

As necessary, antibodies of the present invention may be encapsulated in microcapsules (for example, those made of hydroxymethylcellulose, gelatin, and poly(methylmethacrylate)), or incorporated in colloidal drug delivery systems (for example, liposomes, albumin microspheres, microemulsion, nanoparticles, and nanocapsules) (see, for example, "Remington's Pharmaceutical Science 16th edition", Oslo Ed. (1980)). Methods for preparing the pharmaceutical agents as release-controlled pharmaceutical agents are also well known, and such methods may be applied to the antibodies of the present invention (Langer et al., J. Biomed. Mater. Res. 15: 267-277 (1981); Langer, Chemtech. 12: 98-105 (1982); U.S. Pat. No. 3,773,919; European Patent Application Publication No. EP 58,481; Sidman et al., Biopolymers 22: 547-556 (1983); EP 133,988).

The dose of a pharmaceutical composition of the present invention may be appropriately determined ultimately based on the decision by the physician, considering the type of dosage form, method of administration, patient age and body weight, symptoms of the patient, type of the disease, and degree of progress of the disease. For example, in the case of the above-mentioned bispecific antibody, the dose is approximately 0.001 to approximately 1000 mg/kg per single administration. The dose is preferably approximately 0.01 mg/kg to approximately 100 mg/kg. In the case of the aforementioned bispecific antibody, the administration interval is, for example, at least one day or more. The interval is preferably one week, two weeks, four weeks, one month, three months or six months. These doses may vary depending on the patient's body weight and age, the method of administration, and such; however, appropriate selection of suitable dosage is possible by those skilled in the art. Preferably, the dosing period may also be appropriately determined depending on the therapeutic progress of the patient.

The pharmaceutical compositions of the present invention may be administered either orally or parenterally to patients. Parental administration is preferred. Specifically, such administration methods include injection, nasal administration, transpulmonary administration, and percutaneous administration. Injections include, for example, intravenous injections, intramuscular injections, intraperitoneal injections, and subcutaneous injections.

The pharmaceutical compositions of the present invention can be formulated into oral agents such as granules, powders, tablets, capsules, solutions, emulsions, and suspensions, injections, and such.

Furthermore, the present invention provides genes or nucleic acids encoding the antibodies of the present invention. In addition, gene therapy may be performed by incorporating genes or nucleic acids encoding the antibodies of the present invention into vectors for gene therapy.

Another embodiment of the present invention relates to a method for enhancing activity of an antibody containing a constant region, which is a method of modifying at least one amino acid residue in the constant region. It is preferably a method of modifying at least one amino acid residue in a CH3 region or a hinge region. It is particularly preferably a method of modifying position 434 according to EU numbering, and more preferably a method of modifying Asn (N) at position 434 according to EU numbering to Tyr (Y). It is also particularly preferably a method of modifying the hinge region, and is more preferably a method of modifying positions 216 to 230 according to EU numbering to AAAC (SEQ ID NO: 28). A method of partially modifying positions 216 to 230 according to EU numbering so that positions 216 to 230 according to EU numbering are modified to AAAC is also included in the present invention. Furthermore, as long as the modification mentioned above is included, other modifications may also be included.

Another embodiment of the present invention is a method for enhancing FVIII mimetic activity of a bispecific antibody against FIX and/or FIXa and against FX, which is a method of modifying at least one amino acid residue in the constant region of a bispecific antibody in which an H chain comprising the amino acid sequence of SEQ ID NO: 1 associates with an L chain comprising the amino acid sequence of SEQ ID NO: 3, and an H chain comprising the amino acid sequence of SEQ ID NO: 2 associates with an L chain comprising the amino acid sequence of SEQ ID NO: 3.

Another embodiment of the present invention is a method for enhancing the FVIII mimetic activity of a bispecific antibody against FIX and/or FIXa and FX, which is a method of modifying the amino acid residue at position 434 according to EU numbering to Tyr (Y) in a bispecific antibody in which an H chain comprising the amino acid sequence of SEQ ID NO: 1 associates with an L chain comprising the amino acid sequence of SEQ ID NO: 3, and an H chain comprising the amino acid sequence of SEQ ID NO: 2 associates with an L chain comprising the amino acid sequence of SEQ ID NO: 3.

Another embodiment of the present invention is a method for enhancing the FVIII mimetic activity of a bispecific antibody against FIX and/or FIXa and FX, which is a method of modifying the amino acid residues at positions 216 to 230 according to EU numbering to AAAC in a bispecific antibody in which an H chain comprising the amino acid sequence of SEQ ID NO: 1 associates with an L chain comprising the amino acid sequence of SEQ ID NO: 3, and an H chain comprising the amino acid sequence of SEQ ID NO: 2 associates with an L chain comprising the amino acid sequence of SEQ ID NO: 3.

Another embodiment of the present invention is a method for producing an antibody comprising a constant region, which comprises: (a) modifying at least one amino acid residue in a constant region so that the activity is enhanced compared to the antibody before the modification, by modifying a nucleic acid encoding an antibody comprising the amino acid residue, (b) culturing a host cell to express the nucleic acid, and (c) collecting the antibody from a culture of the host cell.

As used herein, embodiments represented by the expression "comprising . . . " include embodiments represented by the expression "essentially consisting of . . . " and embodiments represented by the expression "consisting of . . . ".

All patents and reference documents explicitly cited herein are incorporated by reference into this specification in their entirety.

The present invention will be further illustrated by the following Examples, but it is not to be construed as being limited thereto.

EXAMPLES

Example 1

ACE910 which is an anti-FIXa/FX bispecific antibody is an antibody having the human IgG4 isotype (J Thromb Haemost. 2014 February; 12(2):206-213). ACE910 (hereinafter, also described as ACE910-A) comprises four chains composed of three types of chains. The anti-FIXa heavy chain is called Q chain, the anti-FX heavy chain is called J chain, and the common light chain is called L chain. ACE910-A (Q, J, and L: SEQ ID NOs: 1, 2, and 3) (WO 2012/067176) was used as the control antibody.

The knobs-into-holes technology (Nat Biotechnol. 1998 July; 16(7):677-81) was used to prepare ACE910 of human IgG1, 2, and 4 types. That is, ACE910-B-IgG1 (Q, J, and L: SEQ ID NOs: 4, 5, and 3), ACE910-B-IgG2 (Q, J, and L: SEQ ID NOs: 6, 7, and 3), and ACE910-B-IgG4 (Q, J, and L: SEQ ID NOs: 8, 9, and 3) were prepared, and effects of the human IgG isotypes on the FVIII mimetic activity were evaluated.

ACE910 is an anti-FIXa/FX bispecific antibody that uses the common L chain (prepared by referring to WO2006/109592) and CH3/CH3 interface regulation (prepared by referring to WO2006/106905). Other methods for preparing bispecific antibodies have been reported (Drug Discov. Today. 2015 Jul. 20(7):838-47; WO2015/046467; WO2011/117329; and WO2013/065708). These methods were used to prepare bispecific antibodies having the variable region sequences of ACE910-A, and the effects of the methods for producing bispecific antibodies on the FVIII mimetic activity were evaluated. More specifically, ACE910-B-IgG4 (Q, J, and L: SEQ ID NOs: 8, 9, and 3), ACE910-D1 (heavy chains Q and J: SEQ ID NOs: 12 and 13) (light chains L1 and L2: SEQ ID NOs: 14 and 15) (prepared by referring to WO2011/117329), ACE910-D2 (heavy chains Q and J: SEQ ID NOs: 16 and 17) (light chains L1 and L2: SEQ ID NOs: 18 and 19) (prepared by referring to WO2011/117329), ACE910-E (heavy chains Q and J: SEQ ID NOs: 20 and 21) (light chains L1 and L2: SEQ ID NOs: 22 and 23) (prepared by referring to WO2013/065708) described below were prepared, and their FVIII mimetic activities were evaluated.

The various ACE910 variants were prepared by methods known to those skilled in the art, such as their total gene syntheses. HEK293FS (Invitrogen) was used for antibody expression, and recombinant Protein A (GE HealthCare) was used for purification, and the bispecific antibodies were prepared by methods known to those skilled in the art.

The FVIII mimetic activities (FXa generation-promoting activities) of the purified bispecific antibodies were measured using the following method. All reactions were performed at room temperature. Five µL of an antibody solution diluted with Tris-buffered saline containing 0.1% bovine serum albumin (hereafter referred to as TBSB) was mixed with 5 µL of 150 ng/mL Human Factor Ixa beta (Enzyme Research Laboratories), and then incubated in a 384-well plate at room temperature for 30 minutes. The enzyme reaction in this mixed solution was initiated by adding 5 µL of 24.7 µg/mL of Human Factor X (Enzyme Research Laboratories). Four minutes later, 5 µL of 0.5 M EDTA was added to stop the reaction. The coloring reaction was initiated by adding 5 µL of coloring substrate solution. After a 30-minute coloring reaction, the change in absorbance at 405 nm was measured using a SpectraMax® 340PC384 microplate reader (Molecular Devices).

The results of comparing the activities of ACE910-B-IgG1 and ACE910-B-IgG4 are shown in FIG. 1. The FVIII mimetic activity was found to be high even for the human IgG1 isotype. In the previous reports, of anti-FIXa/FX bispecific antibodies having FVIII mimetic activities, only the human IgG4 isotypes showed high activities (Patent Documents 1, 2, 3, and 4; and Non-patent Document 7). From the results of this examination, it was found that even the human IgG1 isotype of the anti-FIXa/FX bispecific antibody has high FVIII mimetic activity.

Figure 2:
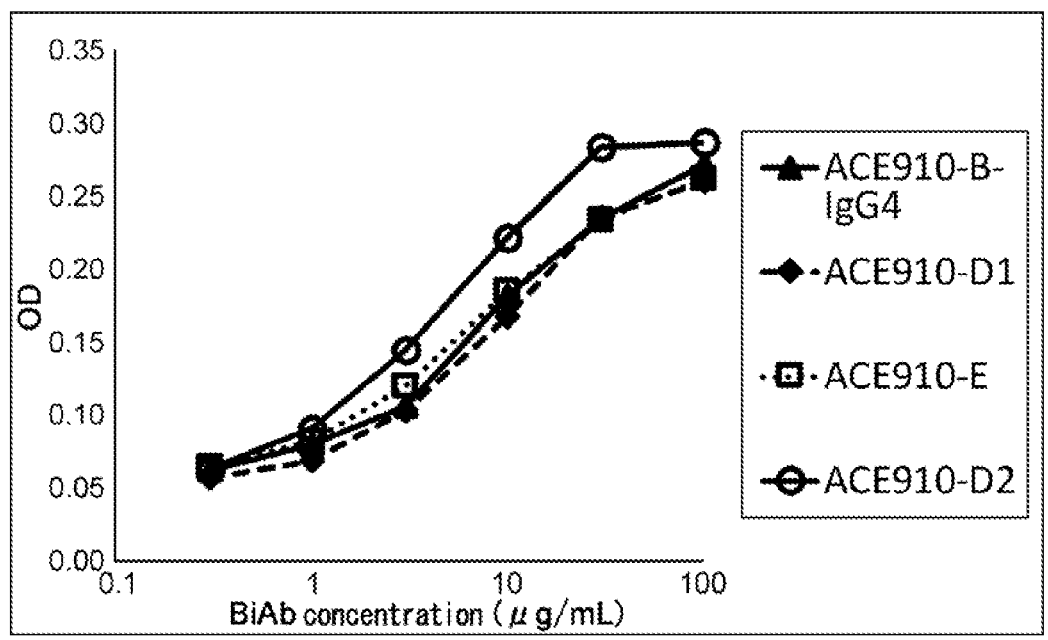
FIG. 2 shows the effects of various bispecific antibody formats on the FVIII mimetic activity of ACE910.

The results of comparing the activities of ACE910-B-IgG4, ACE910-D1, ACE910-D2, and ACE910-E are shown in FIG. 2. The activities of these ACE910 variants were confirmed to be nearly equal to that of ACE910-A, and the FVIII mimetic activity of the variable regions of ACE910 was found to be unaffected by the method for producing bispecific antibodies.

Example 2

Various ACE910 variants were produced by introducing mutations by methods known to those skilled in the art such as total gene synthesis or PCR, into the human IgG4 bispecific antibody ACE910-B-IgG4 (Q, J, and L: SEQ ID NOs: 8, 9, and 3) and ACE910-C(Q, J, and L: SEQ ID NOs: 10, 11, and 3) (prepared by referring to WO2015/046467), which have the same variable region sequence as ACE910-A (Q, J, and L: SEQ ID NOs: 1, 2, and 3). Antibody expression and purification were performed according to the method of Example 1. The introduced mutations are summarized in Table 1 (mutations introduced into regions other than the hinge region) below and in FIG. 5 (mutations introduced into the hinge region).

TABLE 1

| Antibody name | Mutations introduced into the heavy chain |
|---|---|
| T01 | P387R, E388R, Q311R |
| T03 | P387R, D399R, S400R, E345R, H285R |
| T06 | E345R, E430G, S440Y |
| T08 | N434Y |
| T09 | N434W |
| T56 | E345R |
| T57 | S440K |
| QH0001// JH0000 | G26E (Q chain only) |
| QCH0001// JCH0001 | A1621( (Q chain only), N208D (J chain only) |
| T63 | C-terminal sequence of the L chain (SEQ ID NO: 29):- FNRGCE (the mutated sites are underlined) |
| T64 | C-terminal sequence of the L chain (SEQ ID NO: 30):- FNRGEGC (the mutated sites are underlined) |
| T65 | C-terminal sequence of the L chain (SEQ ID NO: 31):- FNRGEGGC (the mutated sites are underlined) |

Figure 3:
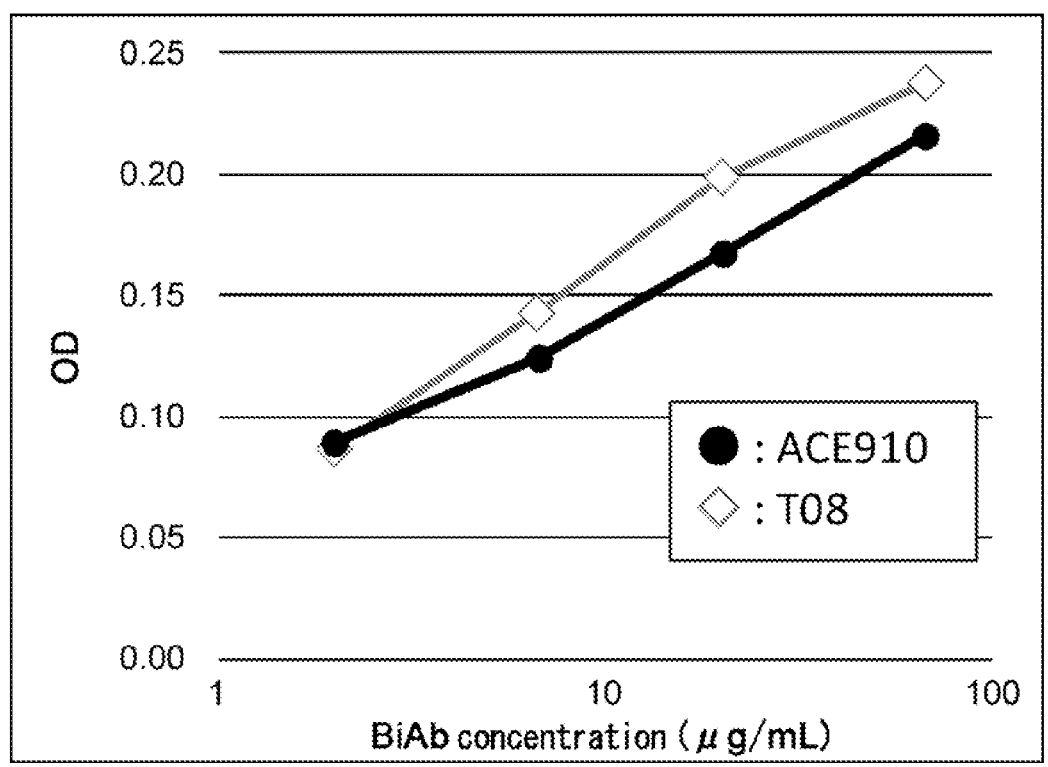
FIG. 3 shows the FVIII mimetic activities of ACE910 and T08.
Figure 4:
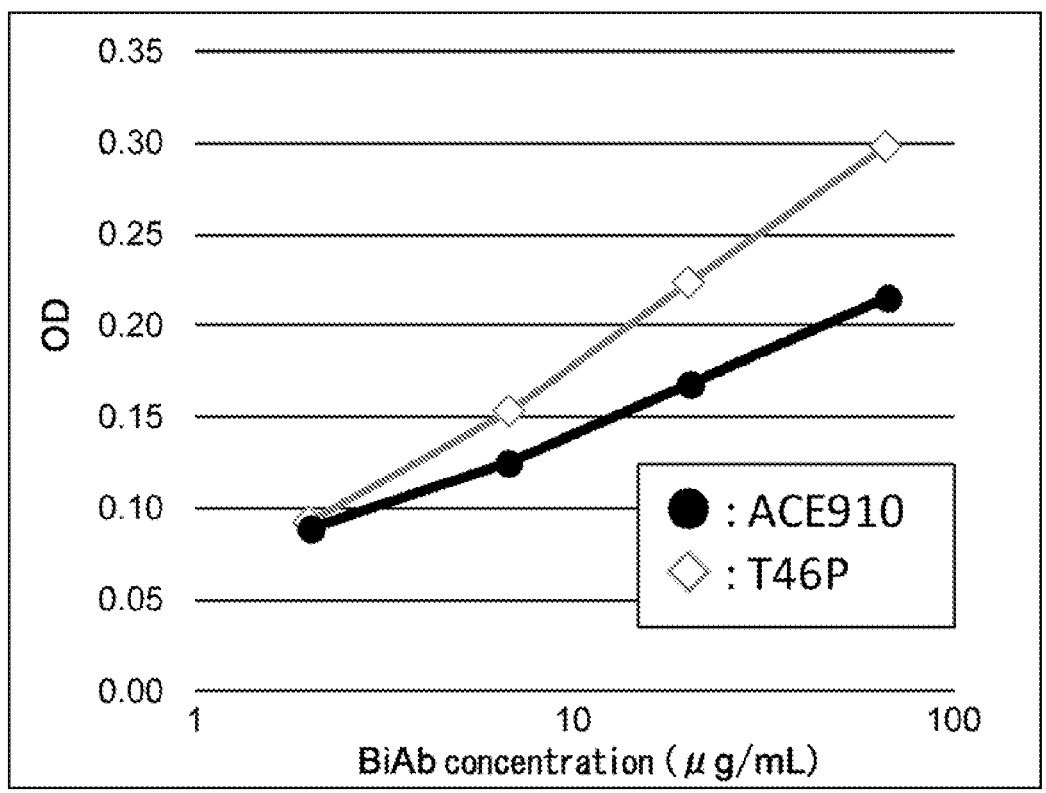
FIG. 4 shows the FVIII mimetic activities of ACE910 and T46P.

Of the various ACE910 variants shown in Table 1 and FIG. 5, T08 (Q, J, and L: SEQ ID 5 NOs: 24, 25, and 3) and T46P (Q, J, and L: SEQ ID NOs:26, 27, and 3) had elevated FVIII mimetic activity compared to the parent antibody ACE910-A. Other ACE910 variants had FVIII mimetic activities equivalent to or lower than that of ACE910. The FVIII mimetic activities of ACE910, T08 and T46P are shown in FIGS. 3 and 4.

The invention claimed is:

1. A bispecific antibody comprising:
   a first heavy chain comprising
   (i) a first heavy chain variable region comprising the heavy chain variable region amino acid sequence of SEQ ID NO: 1 with no modifications, and
   (ii) a first heavy chain constant region comprising the heavy chain constant region amino acid sequence of SEQ ID NO: 1 with no modifications, or with at least one modification in the first heavy chain constant region compared to the heavy chain constant region amino acid sequence of SEQ ID NO: 1;
   a second heavy chain comprising
   (iii) a second heavy chain variable region comprising the heavy chain variable region amino acid sequence of SEQ ID NO: 2 with no modifications, and (iv) a second heavy chain constant region comprising the heavy chain constant region amino acid sequence of SEQ ID NO: 2 with no modifications, or with at least one modification in the second heavy chain constant region compared to the heavy chain constant region amino acid sequence of SEQ ID NO: 2;
a first light chain comprising the amino acid sequence of SEQ ID NO: 3; and
a second light chain comprising the amino acid sequence of SEQ ID NO: 3,
wherein one of the two heavy chain constant regions includes one or both of the following modifications (a) and (b), and the other of the two heavy chain constant regions includes one or both or neither of the following modifications (a) and (b):
(a) a tyrosine (Y) at EU numbering position 434,
(b) the amino acid sequence AAAC replacing the residues at EU numbering positions 216 to 230;
wherein the first heavy chain constant region optionally includes one or more other modifications compared to the heavy chain constant region amino acid sequence of SEQ ID NO: 1;
wherein the second heavy chain constant region optionally includes one or more other modifications compared to the heavy chain constant region amino acid sequence of SEQ ID NO: 2; and
wherein the first heavy chain associates with the first light chain, and the second heavy chain associates with the second light chain.

2. The bispecific antibody of claim 1, wherein the bispecific antibody has higher blood coagulation factor VIII mimetic activity than does a bispecific antibody consisting of:
a heavy chain consisting of the full amino acid sequence of SEQ ID NO: 1, associated with a light chain consisting of the full amino acid sequence of SEQ ID NO: 3; and
a heavy chain consisting of the full amino acid sequence of SEQ ID NO: 2, associated with a light chain consisting of the full amino acid sequence of SEQ ID NO: 3.

3. The bispecific antibody of claim 1, wherein each of the first and second heavy chain constant regions comprises a tyrosine (Y) at EU numbering position 434.

4. The bispecific antibody of claim 3, wherein the amino acid sequence of the first heavy chain constant region further comprises one or more additional modifications compared to the heavy chain constant region amino acid sequence of SEQ ID NO: 1, and the amino acid sequence of the second heavy chain constant region further comprises one or more additional modifications compared to the heavy chain constant region amino acid sequence of SEQ ID NO: 2.

5. The bispecific antibody of claim 4, wherein the first heavy chain comprises the amino acid sequence of SEQ ID NO: 24, and the second heavy chain comprises the amino acid sequence of SEQ ID NO: 25.

6. The bispecific antibody of claim 1, wherein each of the first and second heavy chain constant regions comprises the amino acid sequence AAAC replacing the residues at EU numbering positions 216 to 230 of SEQ ID NOs: 1 and 2, respectively.

7. The bispecific antibody of claim 6, wherein the amino acid sequence of the first heavy chain constant region further comprises one or more additional modifications compared to the heavy chain constant region amino acid sequence of SEQ ID NO: 1, and the amino acid sequence of the second heavy chain constant region further comprises one or more additional modifications compared to the heavy chain constant region amino acid sequence of SEQ ID NO: 2.

8. The bispecific antibody of claim 7, wherein the first heavy chain comprises the amino acid sequence of SEQ ID NO: 26, and the second heavy chain comprises the amino acid sequence of SEQ ID NO: 27.

9. A kit comprising the bispecific antibody of claim 1.

10. A method for treating a subject who has hemophilia A, acquired hemophilia, von Willebrand's disease, or a disease in which an inhibitor of blood coagulation factor VIII and/or activated blood coagulation factor VIII is present, the method comprising administering to the subject a therapeutically effective amount of the bispecific antibody of claim 1.

11. A pharmaceutical composition comprising the bispecific antibody of claim 1 and a pharmaceutically acceptable carrier.

12. A pharmaceutical composition comprising the bispecific antibody of claim 5 and a pharmaceutically acceptable carrier.

13. A pharmaceutical composition comprising the bispecific antibody of claim 8 and a pharmaceutically acceptable carrier.

14. A method for treating bleeding in a subject who has a condition characterized by bleeding due to a deficiency of active blood coagulation factor VIII and/or activated blood coagulation factor VIII, the method comprising administering to the subject a therapeutically effective amount of the bispecific antibody of claim 1.

15. The method of claim 14, wherein the condition is hemophilia A, acquired hemophilia, von Willebrand's disease, or a disease in which an inhibitor of blood coagulation factor VIII and/or activated blood coagulation factor VIII is present.

16. A kit comprising the bispecific antibody of claim 8.

* * * * *

SEQUENCE LISTING

```
<160> NUMBER OF SEQ ID NOS: 75

<210> SEQ ID NO 1
<211> LENGTH: 448
<212> TYPE: PRT
<213> ORGANISM: Artificial Sequence
<220> FEATURE:
<223> OTHER INFORMATION: An artificially synthesized peptide sequence

<400> SEQUENCE: 1

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Gln Trp Val Arg Gln Ala Pro Gly Lys Gly Leu Glu Trp Val
        35                  40                  45

Ser Ser Ile Ser Pro Ser Gly Gln Ser Thr Tyr Tyr Arg Arg Glu Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Gly Arg Glu Tyr Gly Gly Gly Trp Tyr Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160
```

```
Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Leu Gly Thr Gln Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Lys Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Glu Gly Asn Val Phe Ser Cys Ser Val Met His
            420                 425                 430

Glu Ala Leu His Asn Arg Tyr Thr Gln Lys Ser Leu Ser Leu Ser Pro
        435                 440                 445

<210> SEQ ID NO 2
<211> LENGTH: 444
<212> TYPE: PRT
<213> ORGANISM: Artificial Sequence
<220> FEATURE:
<223> OTHER INFORMATION: An artificially synthesized peptide sequence

<400> SEQUENCE: 2

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
            20                  25                  30

Asn Met Asp Trp Val Arg Gln Ala Pro Gly Gln Gly Leu Glu Trp Met
        35                  40                  45

Gly Asp Ile Asn Thr Arg Ser Gly Gly Ser Ile Tyr Asn Glu Glu Phe
    50                  55                  60

Gln Asp Arg Val Ile Met Thr Val Asp Lys Ser Thr Asp Thr Ala Tyr
65                  70                  75                  80
```

```
Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Glu Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Glu Ser Leu Ser Leu Ser Pro
        435                 440
```

<210> SEQ ID NO 3
<211> LENGTH: 214
<212> TYPE: PRT
<213> ORGANISM: Artificial Sequence
<220> FEATURE:
<223> OTHER INFORMATION: An artificially synthesized peptide sequence

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asn Ile Glu Arg Gln
            20                  25                  30

Leu Ala Trp Tyr Gln Gln Lys Pro Gly Gln Ala Pro Glu Leu Leu Ile
            35                  40                  45

Tyr Gln Ala Ser Arg Lys Glu Ser Gly Val Pro Asp Arg Phe Ser Gly
50                  55                  60

Ser Arg Tyr Gly Thr Asp Phe Thr Leu Thr Ile Ser Ser Leu Gln Pro
65                  70                  75                  80

Glu Asp Ile Ala Thr Tyr Tyr Cys Gln Gln Tyr Ser Asp Pro Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 4
<211> LENGTH: 451
<212> TYPE: PRT
<213> ORGANISM: Artificial Sequence
<220> FEATURE:
<223> OTHER INFORMATION: An artificially synthesized peptide sequence

<400> SEQUENCE: 4

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Gln Trp Val Arg Gln Ala Pro Gly Lys Gly Leu Glu Trp Val
            35                  40                  45

Ser Ser Ile Ser Pro Ser Gly Gln Ser Thr Tyr Tyr Arg Arg Glu Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Gly Arg Glu Tyr Gly Gly Trp Tyr Phe Asp Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
        180                 185                 190

Thr Val Pro Ser Ser Ser Leu Gly Thr Gln Thr Tyr Ile Cys Asn Val
    195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Cys Thr Leu Pro Pro Ser Arg Glu Glu Met Thr Lys Asn Gln
        355                 360                 365

Val Ser Leu Trp Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro
    450

<210> SEQ ID NO 5
<211> LENGTH: 447
<212> TYPE: PRT
<213> ORGANISM: Artificial Sequence
<220> FEATURE:
<223> OTHER INFORMATION: An artificially synthesized peptide sequence

<400> SEQUENCE: 5

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
            20                  25                  30

Asn Met Asp Trp Val Arg Gln Ala Pro Gly Gln Gly Leu Glu Trp Met
        35                  40                  45

Gly Asp Ile Asn Thr Arg Ser Gly Gly Ser Ile Tyr Asn Glu Glu Phe
    50                  55                  60

Gln Asp Arg Val Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Glu Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Cys Glu Met Thr Lys Asn Gln Val Ser Leu Ser
        355                 360                 365

Cys Ala Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Pro
        435                 440                 445

<210> SEQ ID NO 6
<211> LENGTH: 448

```
<212> TYPE: PRT
<213> ORGANISM: Artificial Sequence
<220> FEATURE:
<223> OTHER INFORMATION: An artificially synthesized peptide sequence

<400> SEQUENCE: 6

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Gln Trp Val Arg Gln Ala Pro Gly Lys Gly Leu Glu Trp Val
        35                  40                  45

Ser Ser Ile Ser Pro Ser Gly Gln Ser Thr Tyr Tyr Arg Arg Glu Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Arg Thr Gly Arg Glu Tyr Gly Gly Trp Tyr Phe Asp Tyr
        100                 105                 110

Trp Gly Gln Gly Thr Leu Val Thr Val Ser Ser Ala Ser Thr Lys Gly
            115                 120                 125

Pro Ser Val Phe Pro Leu Ala Pro Cys Ser Arg Ser Thr Ser Glu Ser
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
        180                 185                 190

Thr Val Pro Ser Ser Asn Phe Gly Thr Gln Thr Tyr Thr Cys Asn Val
    195                 200                 205

Asp His Lys Pro Ser Asn Thr Lys Val Asp Lys Thr Val Glu Arg Lys
210                 215                 220

Cys Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Gln Phe Asn Trp Tyr Val Asp Gly Val Glu Val His Asn
    275                 280                 285

Ala Lys Thr Lys Pro Arg Glu Glu Gln Phe Asn Ser Thr Phe Arg Val
290                 295                 300

Val Ser Val Leu Thr Val Val His Gln Asp Trp Leu Asn Gly Lys Glu
305                 310                 315                 320

Tyr Lys Cys Lys Val Ser Asn Lys Gly Leu Pro Ala Pro Ile Glu Lys
            325                 330                 335

Thr Ile Ser Lys Thr Lys Gly Gln Pro Arg Glu Pro Gln Val Tyr Thr
        340                 345                 350

Leu Pro Pro Ser Arg Glu Glu Met Thr Lys Asn Gln Val Ser Leu Thr
    355                 360                 365

Cys Leu Val Lys Gly Phe Tyr Pro Ser Asp Ile Ala Val Glu Trp Glu
370                 375                 380
```

Ser Asn Gly Gln Pro Glu Asn Asn Tyr Lys Thr Thr Pro Pro Met Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
            435                 440                 445

<210> SEQ ID NO 7
<211> LENGTH: 443
<212> TYPE: PRT
<213> ORGANISM: Artificial Sequence
<220> FEATURE:
<223> OTHER INFORMATION: An artificially synthesized peptide sequence

<400> SEQUENCE: 7

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
            20                  25                  30

Asn Met Asp Trp Val Arg Gln Ala Pro Gly Gln Gly Leu Glu Trp Met
        35                  40                  45

Gly Asp Ile Asn Thr Arg Ser Gly Gly Ser Ile Tyr Asn Glu Glu Phe
    50                  55                  60

Gln Asp Arg Val Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Glu Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

```
Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
            325                 330                 335

Thr Lys Gly Gln Pro Arg Glu Pro Gln Val Tyr Thr Leu Pro Pro Ser
            340                 345                 350

Arg Cys Glu Met Thr Lys Asn Gln Val Ser Leu Ser Cys Ala Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Met Leu Asp Ser Asp Gly
385                 390                 395                 400

Ser Phe Phe Leu Val Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro
            435                 440
```

<210> SEQ ID NO 8
<211> LENGTH: 448
<212> TYPE: PRT
<213> ORGANISM: Artificial Sequence
<220> FEATURE:
<223> OTHER INFORMATION: An artificially synthesized peptide sequence

<400> SEQUENCE: 8

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Gln Trp Val Arg Gln Ala Pro Gly Lys Gly Leu Glu Trp Val
            35                  40                  45

Ser Ser Ile Ser Pro Ser Gly Gln Ser Thr Tyr Tyr Arg Arg Glu Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Gly Arg Glu Tyr Gly Gly Trp Tyr Phe Asp Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Thr Cys Asn Val
            195                 200                 205

Asp His Lys Pro Ser Asn Thr Lys Val Asp Lys Arg Val Glu Ser Lys
    210                 215                 220
```

```
Tyr Gly Pro Pro Cys Pro Pro Cys Pro Ala Pro Glu Phe Arg Arg Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser Gln Glu
        260                 265                 270

Asp Pro Glu Val Gln Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
            325                 330                 335

Lys Thr Ile Ser Lys Ala Lys Gly Gln Pro Arg Glu Pro Gln Val Cys
        340                 345                 350

Thr Leu Pro Pro Ser Gln Glu Glu Met Thr Lys Asn Gln Val Ser Leu
    355                 360                 365

Trp Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
            405                 410                 415

Lys Ser Arg Trp Gln Glu Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

<210> SEQ ID NO 9
<211> LENGTH: 444
<212> TYPE: PRT
<213> ORGANISM: Artificial Sequence
<220> FEATURE:
<223> OTHER INFORMATION: An artificially synthesized peptide sequence

<400> SEQUENCE: 9

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
            20                  25                  30

Asn Met Asp Trp Val Arg Gln Ala Pro Gly Gln Gly Leu Glu Trp Met
        35                  40                  45

Gly Asp Ile Asn Thr Arg Ser Gly Gly Ser Ile Tyr Asn Glu Glu Phe
    50                  55                  60

Gln Asp Arg Val Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
            85                  90                  95

Ala Arg Arg Lys Ser Tyr Gly Tyr Tyr Leu Asp Glu Trp Gly Glu Gly
        100                 105                 110

Thr Leu Val Thr Val Ser Ser Ala Ser Thr Lys Gly Pro Ser Val Phe
    115                 120                 125

Pro Leu Ala Pro Cys Ser Arg Ser Thr Ser Glu Ser Thr Ala Ala Leu
130                 135                 140
```

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Arg Arg Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Gln Cys Glu Met Thr Lys Asn Gln Val Ser Leu Ser Cys Ala Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Val Ser Arg Leu Thr Val Asp Lys Ser Arg Trp
                405                 410                 415

Gln Glu Gly Asn Val Phe Ser Cys Ser Val Met His Glu Ala Leu His
                420                 425                 430

Asn His Tyr Thr Gln Lys Ser Leu Ser Leu Ser Pro
            435                 440

<210> SEQ ID NO 10
<211> LENGTH: 448
<212> TYPE: PRT
<213> ORGANISM: Artificial Sequence
<220> FEATURE:
<223> OTHER INFORMATION: An artificially synthesized peptide sequence

<400> SEQUENCE: 10

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Gln Trp Val Arg Gln Ala Pro Gly Lys Gly Leu Glu Trp Val
        35                  40                  45

Ser Ser Ile Ser Pro Ser Gly Gln Ser Thr Tyr Tyr Arg Arg Glu Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Arg Thr Gly Arg Glu Tyr Gly Gly Trp Tyr Phe Asp Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Cys Ser Arg Ser Thr Ser Glu Ser
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Thr Cys Asn Val
            195                 200                 205

Asp His Lys Pro Ser Asn Thr Lys Val Asp Lys Arg Val Glu Ser Lys
210                 215                 220

Tyr Gly Pro Pro Cys Pro Pro Cys Pro Ala Pro Glu Phe Arg Arg Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Lys Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

<210> SEQ ID NO 11
<211> LENGTH: 444
<212> TYPE: PRT
<213> ORGANISM: Artificial Sequence
<220> FEATURE:
<223> OTHER INFORMATION: An artificially synthesized peptide sequence
```

<400> SEQUENCE: 11

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
            20                  25                  30

Asn Met Asp Trp Val Arg Gln Ala Pro Gly Gln Gly Leu Glu Trp Met
        35                  40                  45

Gly Asp Ile Asn Thr Arg Ser Gly Gly Ser Ile Tyr Asn Glu Glu Phe
50                  55                  60

Gln Asp Arg Val Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Glu Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Thr Cys Asn Val Asp His Lys Pro
        195                 200                 205

Ser Asn Thr Lys Val Asp Lys Arg Val Glu Ser Lys Tyr Gly Pro Pro
210                 215                 220

Cys Pro Pro Cys Pro Ala Pro Glu Phe Arg Arg Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
```

```
                    405                 410                 415
Gln Glu Gly Asn Val Phe Ser Cys Ser Val Met His Glu Ala Leu His
            420                 425                 430

Asn His Tyr Thr Gln Glu Ser Leu Ser Leu Ser Pro
        435                 440

<210> SEQ ID NO 12
<211> LENGTH: 434
<212> TYPE: PRT
<213> ORGANISM: Artificial Sequence
<220> FEATURE:
<223> OTHER INFORMATION: An artificially synthesized peptide sequence

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asn Ile Glu Arg Gln
            20                  25                  30

Leu Ala Trp Tyr Gln Gln Lys Pro Gly Gln Ala Pro Glu Leu Leu Ile
        35                  40                  45

Tyr Gln Ala Ser Arg Lys Glu Ser Gly Val Pro Asp Arg Phe Ser Gly
50                  55                  60

Ser Arg Tyr Gly Thr Asp Phe Thr Leu Thr Ile Ser Ser Leu Gln Pro
65                  70                  75                  80

Glu Asp Ile Ala Thr Tyr Tyr Cys Gln Gln Tyr Ser Asp Pro Pro Leu
                85                  90                  95

Thr Phe Gly Gly Gly Thr Lys Val Glu Ile Lys Ser Ser Ala Ser Thr
            100                 105                 110

Lys Gly Pro Ser Val Phe Pro Leu Ala Pro Cys Ser Arg Ser Thr Ser
        115                 120                 125

Glu Ser Thr Ala Ala Leu Gly Cys Leu Val Lys Asp Tyr Phe Pro Glu
130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Thr Cys
            180                 185                 190

Asn Val Asp His Lys Pro Ser Asn Thr Lys Val Asp Lys Arg Val Glu
        195                 200                 205

Ser Lys Tyr Gly Pro Pro Cys Pro Pro Cys Pro Ala Pro Glu Phe Arg
210                 215                 220

Arg Gly Pro Ser Val Phe Leu Phe Pro Pro Lys Pro Lys Asp Thr Leu
225                 230                 235                 240

Met Ile Ser Arg Thr Pro Glu Val Thr Cys Val Val Val Asp Val Ser
                245                 250                 255

Gln Glu Asp Pro Glu Val Gln Phe Asn Trp Tyr Val Asp Gly Val Glu
            260                 265                 270

Val His Asn Ala Lys Thr Lys Pro Arg Glu Glu Gln Tyr Asn Ser Thr
        275                 280                 285

Tyr Arg Val Val Ser Val Leu Thr Val Leu His Gln Asp Trp Leu Asn
290                 295                 300

Gly Lys Glu Tyr Lys Cys Lys Val Ser Asn Lys Gly Leu Pro Ser Ser
305                 310                 315                 320

Ile Glu Lys Thr Ile Ser Lys Ala Lys Gly Gln Pro Arg Glu Pro Gln
```

```
                    325                 330                 335
Val Cys Thr Leu Pro Ser Gln Glu Glu Met Thr Lys Asn Gln Val
                340                 345                 350

Ser Leu Trp Cys Leu Val Lys Gly Phe Tyr Pro Ser Asp Ile Ala Val
            355                 360                 365

Glu Trp Glu Ser Asn Gly Gln Pro Glu Asn Asn Tyr Lys Thr Thr Pro
    370                 375                 380

Pro Val Leu Asp Ser Asp Gly Ser Phe Phe Leu Tyr Ser Arg Leu Thr
385                 390                 395                 400

Val Asp Lys Ser Arg Trp Gln Glu Gly Asn Val Phe Ser Cys Ser Val
                405                 410                 415

Met His Glu Ala Leu His Asn His Tyr Thr Gln Lys Ser Leu Ser Leu
                420                 425                 430

Ser Pro

<210> SEQ ID NO 13
<211> LENGTH: 444
<212> TYPE: PRT
<213> ORGANISM: Artificial Sequence
<220> FEATURE:
<223> OTHER INFORMATION: An artificially synthesized peptide sequence

<400> SEQUENCE: 13

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
            20                  25                  30

Asn Met Asp Trp Val Arg Gln Ala Pro Gly Gln Gly Leu Glu Trp Met
        35                  40                  45

Gly Asp Ile Asn Thr Arg Ser Gly Gly Ser Ile Tyr Asn Glu Glu Phe
    50                  55                  60

Gln Asp Arg Val Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Glu Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Arg Arg Gly Pro Ser Val Phe
225                 230                 235                 240

Leu Phe Pro Pro Lys Pro Lys Asp Thr Leu Met Ile Ser Arg Thr Pro
                245                 250                 255
```

```
Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Cys Glu Met Thr Lys Asn Gln Val Ser Leu Ser Cys Ala Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Val Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Pro
        435                 440

<210> SEQ ID NO 14
<211> LENGTH: 230
<212> TYPE: PRT
<213> ORGANISM: Artificial Sequence
<220> FEATURE:
<223> OTHER INFORMATION: An artificially synthesized peptide sequence

<400> SEQUENCE: 14

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Gln Trp Val Arg Gln Ala Pro Gly Lys Gly Leu Glu Trp Val
        35                  40                  45

Ser Ser Ile Ser Pro Ser Gly Gln Ser Thr Tyr Tyr Arg Arg Glu Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Gly Arg Glu Tyr Gly Gly Gly Trp Tyr Phe Asp Tyr
            100                 105                 110

Trp Gly Gln Gly Thr Leu Val Thr Val Ser Ser Ala Ser Val Ala Ala
        115                 120                 125

Pro Ser Val Phe Ile Phe Pro Pro Ser Asp Glu Gln Leu Lys Ser Gly
    130                 135                 140

Thr Ala Ser Val Val Cys Leu Leu Asn Asn Phe Tyr Pro Arg Glu Ala
145                 150                 155                 160

Lys Val Gln Trp Lys Val Asp Asn Ala Leu Gln Ser Gly Asn Ser Gln
                165                 170                 175
```

```
Glu Ser Val Thr Glu Gln Asp Ser Lys Asp Ser Thr Tyr Ser Leu Ser
            180                 185                 190

Ser Thr Leu Thr Leu Ser Lys Ala Asp Tyr Glu Lys His Lys Val Tyr
            195                 200                 205

Ala Cys Glu Val Thr His Gln Gly Leu Ser Ser Pro Val Thr Lys Ser
210                 215                 220

Phe Asn Arg Gly Glu Cys
225             230

<210> SEQ ID NO 15
<211> LENGTH: 214
<212> TYPE: PRT
<213> ORGANISM: Artificial Sequence
<220> FEATURE:
<223> OTHER INFORMATION: An artificially synthesized peptide sequence

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asn Ile Glu Arg Gln
            20                  25                  30

Leu Ala Trp Tyr Gln Gln Lys Pro Gly Gln Ala Pro Glu Leu Leu Ile
        35                  40                  45

Tyr Gln Ala Ser Arg Lys Glu Ser Gly Val Pro Asp Arg Phe Ser Gly
    50                  55                  60

Ser Arg Tyr Gly Thr Asp Phe Thr Leu Thr Ile Ser Ser Leu Gln Pro
65                  70                  75                  80

Glu Asp Ile Ala Thr Tyr Tyr Cys Gln Gln Tyr Ser Asp Pro Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 16
<211> LENGTH: 452
<212> TYPE: PRT
<213> ORGANISM: Artificial Sequence
<220> FEATURE:
<223> OTHER INFORMATION: An artificially synthesized peptide sequence

<400> SEQUENCE: 16

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
```

```
                    20                  25                  30
Asp Ile Gln Trp Val Arg Gln Ala Pro Gly Lys Gly Leu Glu Trp Val
                35                  40                  45

Ser Ser Ile Ser Pro Ser Gly Gln Ser Thr Tyr Tyr Arg Arg Glu Val
            50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Gly Arg Glu Tyr Gly Gly Gly Trp Tyr Phe Asp Tyr
                100                 105                 110

Trp Gly Gln Gly Thr Leu Val Thr Val Ser Ser Ala Ser Val Ala Ala
                115                 120                 125

Pro Ser Val Phe Ile Phe Pro Ser Asp Glu Gln Leu Lys Ser Gly
            130                 135                 140

Thr Ala Ser Val Val Cys Leu Leu Asn Asn Phe Tyr Pro Arg Glu Ala
145                 150                 155                 160

Lys Val Gln Trp Lys Val Asp Asn Ala Leu Gln Ser Gly Asn Ser Gln
                165                 170                 175

Glu Ser Val Thr Glu Gln Asp Ser Lys Asp Ser Thr Tyr Ser Leu Ser
                180                 185                 190

Ser Thr Leu Thr Leu Ser Lys Ala Asp Tyr Glu Lys His Lys Val Tyr
            195                 200                 205

Ala Cys Glu Val Thr His Gln Gly Leu Ser Ser Pro Val Thr Lys Ser
        210                 215                 220

Phe Asn Arg Gly Glu Cys Pro Pro Cys Pro Ala Pro Glu
225                 230                 235                 240

Phe Arg Arg Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser Gln Glu Asp Pro Glu Val Gln Phe Asn Trp Tyr Val Asp Gly
            275                 280                 285

Val Glu Val His Asn Ala Lys Thr Lys Pro Arg Glu Glu Gln Tyr Asn
        290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Gly Leu Pro
                325                 330                 335

Ser Ser Ile Glu Lys Thr Ile Ser Lys Ala Lys Gly Gln Pro Arg Glu
            340                 345                 350

Pro Gln Val Cys Thr Leu Pro Pro Ser Gln Glu Glu Met Thr Lys Asn
        355                 360                 365

Gln Val Ser Leu Trp Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Arg
                405                 410                 415

Leu Thr Val Asp Lys Ser Arg Trp Gln Glu Gly Asn Val Phe Ser Cys
            420                 425                 430

Ser Val Met His Glu Ala Leu His Asn His Tyr Thr Gln Lys Ser Leu
        435                 440                 445
```

-continued

Ser Leu Ser Pro
    450

<210> SEQ ID NO 17
<211> LENGTH: 444
<212> TYPE: PRT
<213> ORGANISM: Artificial Sequence
<220> FEATURE:
<223> OTHER INFORMATION: An artificially synthesized peptide sequence

<400> SEQUENCE: 17

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
                20                  25                  30

Asn Met Asp Trp Val Arg Gln Ala Pro Gly Gln Gly Leu Glu Trp Met
            35                  40                  45

Gly Asp Ile Asn Thr Arg Ser Gly Gly Ser Ile Tyr Asn Glu Glu Phe
        50                  55                  60

Gln Asp Arg Val Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Glu Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Arg Arg Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

```
Ser Gln Cys Glu Met Thr Lys Asn Gln Val Ser Leu Ser Cys Ala Val
        355                 360                 365

Lys Gly Phe Tyr Pro Ser Asp Ile Ala Val Glu Trp Glu Ser Asn Gly
    370                 375                 380

Gln Pro Glu Asn Tyr Lys Thr Thr Pro Pro Val Leu Asp Ser Asp
385                 390                 395                 400

Gly Ser Phe Phe Leu Val Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Pro
        435                 440

<210> SEQ ID NO 18
<211> LENGTH: 212
<212> TYPE: PRT
<213> ORGANISM: Artificial Sequence
<220> FEATURE:
<223> OTHER INFORMATION: An artificially synthesized peptide sequence

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asn Ile Glu Arg Gln
            20                  25                  30

Leu Ala Trp Tyr Gln Gln Lys Pro Gly Gln Ala Pro Glu Leu Leu Ile
        35                  40                  45

Tyr Gln Ala Ser Arg Lys Glu Ser Gly Val Pro Asp Arg Phe Ser Gly
    50                  55                  60

Ser Arg Tyr Gly Thr Asp Phe Thr Leu Thr Ile Ser Ser Leu Gln Pro
65                  70                  75                  80

Glu Asp Ile Ala Thr Tyr Tyr Cys Gln Gln Tyr Ser Asp Pro Pro Leu
                85                  90                  95

Thr Phe Gly Gly Gly Thr Lys Val Glu Ile Lys Ser Ser Ala Ser Thr
            100                 105                 110

Lys Gly Pro Ser Val Phe Pro Leu Ala Pro Cys Ser Arg Ser Thr Ser
        115                 120                 125

Glu Ser Thr Ala Ala Leu Gly Cys Leu Val Lys Asp Tyr Phe Pro Glu
    130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Thr Cys
            180                 185                 190

Asn Val Asp His Lys Pro Ser Asn Thr Lys Val Asp Lys Arg Val Glu
        195                 200                 205

Ser Lys Tyr Gly
    210

<210> SEQ ID NO 19
<211> LENGTH: 214
<212> TYPE: PRT
<213> ORGANISM: Artificial Sequence
<220> FEATURE:
<223> OTHER INFORMATION: An artificially synthesized peptide sequence
```

```
<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asn Ile Glu Arg Gln
            20                  25                  30

Leu Ala Trp Tyr Gln Gln Lys Pro Gly Gln Ala Pro Glu Leu Leu Ile
        35                  40                  45

Tyr Gln Ala Ser Arg Lys Glu Ser Gly Val Pro Asp Arg Phe Ser Gly
    50                  55                  60

Ser Arg Tyr Gly Thr Asp Phe Thr Leu Thr Ile Ser Ser Leu Gln Pro
65                  70                  75                  80

Glu Asp Ile Ala Thr Tyr Tyr Cys Gln Gln Tyr Ser Asp Pro Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 20
<211> LENGTH: 448
<212> TYPE: PRT
<213> ORGANISM: Artificial Sequence
<220> FEATURE:
<223> OTHER INFORMATION: An artificially synthesized peptide sequence

<400> SEQUENCE: 20

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Gln Trp Val Arg Lys Ala Pro Gly Lys Gly Leu Glu Trp Val
        35                  40                  45

Ser Ser Ile Ser Pro Ser Gly Gln Ser Thr Tyr Tyr Arg Arg Glu Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Gly Arg Glu Tyr Gly Gly Trp Tyr Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
```

```
                130                 135                 140
Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Lys Ser Ser Gly Leu Tyr Ser Leu Ser Ser Val Val
            180                 185                 190

Thr Val Pro Ser Ser Ser Leu Gly Thr Gln Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Cys Pro Ala Pro Glu Phe Arg Arg Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Cys
            340                 345                 350

Thr Leu Pro Pro Ser Gln Glu Met Thr Lys Asn Gln Val Ser Leu
        355                 360                 365

Trp Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

<210> SEQ ID NO 21
<211> LENGTH: 444
<212> TYPE: PRT
<213> ORGANISM: Artificial Sequence
<220> FEATURE:
<223> OTHER INFORMATION: An artificially synthesized peptide sequence

<400> SEQUENCE: 21

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
            20                  25                  30

Asn Met Asp Trp Val Arg Glu Ala Pro Gly Gln Gly Leu Glu Trp Met
        35                  40                  45

Gly Asp Ile Asn Thr Arg Ser Gly Gly Ser Ile Tyr Asn Glu Glu Phe
```

```
                50                  55                  60
Gln Asp Arg Val Ile Met Thr Val Asp Lys Ser Thr Asp Thr Ala Tyr
 65                  70                  75                  80
Met Glu Leu Ser Ser Leu Arg Ser Glu Asp Thr Ala Thr Tyr His Cys
                 85                  90                  95
Ala Arg Arg Lys Ser Tyr Gly Tyr Tyr Leu Asp Glu Trp Gly Glu Gly
                100                 105                 110
Thr Leu Val Thr Val Ser Ser Ala Ser Thr Lys Gly Pro Ser Val Phe
                115                 120                 125
Pro Leu Ala Pro Cys Ser Arg Ser Thr Ser Glu Ser Thr Ala Ala Leu
130                 135                 140
Gly Cys Leu Val Glu Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Glu Ser Ser Gly Leu Tyr Ser Leu Ser Ser Val Val Thr Val Pro Ser
                180                 185                 190
Ser Ser Leu Gly Thr Gln Thr Tyr Thr Cys Asn Val Asp His Lys Pro
                195                 200                 205
Ser Asn Thr Lys Val Asp Glu Arg Val Glu Ser Lys Tyr Gly Pro Pro
210                 215                 220
Cys Pro Pro Cys Pro Ala Pro Glu Phe Arg Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser Gln Glu Asp Pro Glu Val
                260                 265                 270
Gln Phe Asn Trp Tyr Val Asp Gly Val Glu Val His Asn Ala Lys Thr
                275                 280                 285
Lys Pro Arg Glu Glu Gln Tyr Asn Ser Thr Tyr Arg Val Val Ser Val
290                 295                 300
Leu Thr Val Leu His Gln Asp Trp Leu Asn Gly Lys Glu Tyr Lys Cys
305                 310                 315                 320
Lys Val Ser Asn Lys Gly Leu Pro Ser Ser Ile Glu Lys Thr Ile Ser
                325                 330                 335
Lys Ala Lys Gly Gln Pro Arg Glu Pro Gln Val Tyr Thr Leu Pro Pro
                340                 345                 350
Ser Gln Cys Glu Met Thr Lys Asn Gln Val Ser Leu Ser Cys Ala Val
                355                 360                 365
Lys Gly Phe Tyr Pro Ser Asp Ile Ala Val Glu Trp Glu Ser Asn Gly
                370                 375                 380
Gln Pro Glu Asn Asn Tyr Lys Thr Thr Pro Pro Val Leu Asp Ser Asp
385                 390                 395                 400
Gly Ser Phe Phe Leu Val Ser Arg Leu Thr Val Asp Lys Ser Arg Trp
                405                 410                 415
Gln Glu Gly Asn Val Phe Ser Cys Ser Val Met His Glu Ala Leu His
                420                 425                 430
Asn His Tyr Thr Gln Lys Ser Leu Ser Leu Ser Pro
                435                 440

<210> SEQ ID NO 22
<211> LENGTH: 214
<212> TYPE: PRT
<213> ORGANISM: Artificial Sequence
```

-continued

```
<220> FEATURE:
<223> OTHER INFORMATION: An artificially synthesized peptide sequence

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asn Ile Glu Arg Gln
                20                  25                  30

Leu Ala Trp Tyr Gln Glu Lys Pro Gly Gln Ala Pro Glu Leu Leu Ile
            35                  40                  45

Tyr Gln Ala Ser Arg Lys Glu Ser Gly Val Pro Asp Arg Phe Ser Gly
50                  55                  60

Ser Arg Tyr Gly Thr Asp Phe Thr Leu Thr Ile Ser Ser Leu Gln Pro
65                  70                  75                  80

Glu Asp Ile Ala Thr Tyr Tyr Cys Gln Gln Tyr Ser Asp Pro Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Glu Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Glu
145                 150                 155                 160

Glu Ser Val Thr Glu Gln Asp Ser Lys Asp Ser Thr Tyr Ser Leu Ser
                165                 170                 175

Ser Thr Leu Glu Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 23
<211> LENGTH: 214
<212> TYPE: PRT
<213> ORGANISM: Artificial Sequence
<220> FEATURE:
<223> OTHER INFORMATION: An artificially synthesized peptide sequence

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asn Ile Glu Arg Gln
                20                  25                  30

Leu Ala Trp Tyr Gln Lys Lys Pro Gly Gln Ala Pro Glu Leu Leu Ile
            35                  40                  45

Tyr Gln Ala Ser Arg Lys Glu Ser Gly Val Pro Asp Arg Phe Ser Gly
50                  55                  60

Ser Arg Tyr Gly Thr Asp Phe Thr Leu Thr Ile Ser Ser Leu Gln Pro
65                  70                  75                  80

Glu Asp Ile Ala Thr Tyr Tyr Cys Gln Gln Tyr Ser Asp Pro Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
```

```
            115                 120                 125
Thr Ala Lys Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Lys
145                 150                 155                 160

Glu Ser Val Thr Glu Gln Asp Ser Lys Asp Ser Thr Tyr Ser Leu Ser
                165                 170                 175

Ser Thr Leu Lys Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 24
<211> LENGTH: 448
<212> TYPE: PRT
<213> ORGANISM: Artificial Sequence
<220> FEATURE:
<223> OTHER INFORMATION: An artificially synthesized peptide sequence

<400> SEQUENCE: 24

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Gln Trp Val Arg Gln Ala Pro Gly Lys Gly Leu Glu Trp Val
        35                  40                  45

Ser Ser Ile Ser Pro Ser Gly Gln Ser Thr Tyr Tyr Arg Arg Glu Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Gly Arg Glu Tyr Gly Gly Gly Trp Tyr Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Arg Arg Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
```

```
                  260                 265                 270
Asp Pro Glu Val Gln Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
        290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Gly Leu Pro Ser Ser Ile Glu
                325                 330                 335
Lys Thr Ile Ser Lys Ala Lys Gly Gln Pro Arg Glu Pro Gln Val Cys
            340                 345                 350
Thr Leu Pro Pro Ser Gln Glu Glu Met Thr Lys Asn Gln Val Ser Leu
        355                 360                 365
Trp Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Arg Leu Thr Val Asp
                405                 410                 415
Lys Ser Arg Trp Gln Glu Gly Asn Val Phe Ser Cys Ser Val Met His
            420                 425                 430
Glu Ala Leu His Tyr His Tyr Thr Gln Lys Ser Leu Ser Leu Ser Pro
        435                 440                 445

<210> SEQ ID NO 25
<211> LENGTH: 444
<212> TYPE: PRT
<213> ORGANISM: Artificial Sequence
<220> FEATURE:
<223> OTHER INFORMATION: An artificially synthesized peptide sequence

<400> SEQUENCE: 25

Gln Val Gln Leu Val Gln Ser Gly Ser Glu Leu Lys Lys Pro Gly Ala
1               5                   10                  15
Ser Val Lys Val Ser Cys Lys Ala Ser Gly Tyr Thr Phe Thr Asp Asn
            20                  25                  30
Asn Met Asp Trp Val Arg Gln Ala Pro Gly Gln Gly Leu Glu Trp Met
        35                  40                  45
Gly Asp Ile Asn Thr Arg Ser Gly Gly Ser Ile Tyr Asn Glu Glu Phe
    50                  55                  60
Gln Asp Arg Val Ile Met Thr Val Asp Lys Ser Thr Asp Thr Ala Tyr
65                  70                  75                  80
Met Glu Leu Ser Ser Leu Arg Ser Glu Asp Thr Ala Thr Tyr His Cys
                85                  90                  95
Ala Arg Arg Lys Ser Tyr Gly Tyr Tyr Leu Asp Glu Trp Gly Glu Gly
            100                 105                 110
Thr Leu Val Thr Val Ser Ser Ala Ser Thr Lys Gly Pro Ser Val Phe
        115                 120                 125
Pro Leu Ala Pro Cys Ser Arg Ser Thr Ser Glu Ser Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
```

```
                180             185             190
Ser Ser Leu Gly Thr Gln Thr Tyr Thr Cys Asn Val Asp His Lys Pro
            195                 200                 205
Ser Asn Thr Lys Val Asp Lys Arg Val Glu Ser Lys Tyr Gly Pro Pro
        210                 215                 220
Cys Pro Pro Cys Pro Ala Pro Glu Phe Arg Arg Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser Gln Glu Asp Pro Glu Val
            260                 265                 270
Gln Phe Asn Trp Tyr Val Asp Gly Val Glu Val His Asn Ala Lys Thr
        275                 280                 285
Lys Pro Arg Glu Glu Gln Tyr Asn Ser Thr Tyr Arg Val Val Ser Val
        290                 295                 300
Leu Thr Val Leu His Gln Asp Trp Leu Asn Gly Lys Glu Tyr Lys Cys
305                 310                 315                 320
Lys Val Ser Asn Lys Gly Leu Pro Ser Ser Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Gln Cys Glu Met Thr Lys Asn Gln Val Ser Leu Ser Cys Ala Val
        355                 360                 365
Lys Gly Phe Tyr Pro Ser Asp Ile Ala Val Glu Trp Glu Ser Asn Gly
        370                 375                 380
Gln Pro Glu Asn Asn Tyr Lys Thr Thr Pro Pro Val Leu Asp Ser Asp
385                 390                 395                 400
Gly Ser Phe Phe Leu Val Ser Arg Leu Thr Val Asp Lys Ser Arg Trp
                405                 410                 415
Gln Glu Gly Asn Val Phe Ser Cys Ser Val Met His Glu Ala Leu His
            420                 425                 430
Tyr His Tyr Thr Gln Lys Ser Leu Ser Leu Ser Pro
            435                 440

<210> SEQ ID NO 26
<211> LENGTH: 440
<212> TYPE: PRT
<213> ORGANISM: Artificial Sequence
<220> FEATURE:
<223> OTHER INFORMATION: An artificially synthesized peptide sequence

<400> SEQUENCE: 26

Gln Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Tyr Tyr
            20                  25                  30
Asp Ile Gln Trp Val Arg Gln Ala Pro Gly Lys Gly Leu Glu Trp Val
        35                  40                  45
Ser Ser Ile Ser Pro Ser Gly Gln Ser Thr Tyr Tyr Arg Arg Glu Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Arg Thr Gly Arg Glu Tyr Gly Gly Gly Trp Tyr Phe Asp Tyr
```

```
            100                 105                 110
Trp Gly Gln Gly Thr Leu Val Thr Val Ser Ser Ala Ser Thr Lys Gly
            115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Thr Cys Asn Val
        195                 200                 205

Asp His Lys Pro Ser Asn Thr Lys Val Asp Lys Arg Val Ala Ala Ala
    210                 215                 220

Cys Ala Pro Glu Phe Arg Arg Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Cys Thr Leu Pro Pro Ser Gln Glu Glu
            340                 345                 350

Met Thr Lys Asn Gln Val Ser Leu Trp Cys Leu Val Lys Gly Phe Tyr
        355                 360                 365

Pro Ser Asp Ile Ala Val Glu Trp Glu Ser Asn Gly Gln Pro Glu Asn
    370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro
        435                 440

<210> SEQ ID NO 27
<211> LENGTH: 436
<212> TYPE: PRT
<213> ORGANISM: Artificial Sequence
<220> FEATURE:
<223> OTHER INFORMATION: An artificially synthesized peptide sequence

<400> SEQUENCE: 27

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
```

```
            20                  25                  30
Asn Met Asp Trp Val Arg Gln Ala Pro Gly Gln Gly Leu Glu Trp Met
        35                  40                  45
Gly Asp Ile Asn Thr Arg Ser Gly Ser Ile Tyr Asn Glu Glu Phe
    50                  55                  60
Gln Asp Arg Val Ile Met Thr Val Asp Lys Ser Thr Asp Thr Ala Tyr
65                  70                  75                  80
Met Glu Leu Ser Ser Leu Arg Ser Glu Asp Thr Ala Thr Tyr His Cys
                85                  90                  95
Ala Arg Arg Lys Ser Tyr Gly Tyr Tyr Leu Asp Glu Trp Gly Glu Gly
            100                 105                 110
Thr Leu Val Thr Val Ser Ser Ala Ser Thr Lys Gly Pro Ser Val Phe
        115                 120                 125
Pro Leu Ala Pro Cys Ser Arg Ser Thr Ser Glu Ser Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Thr Cys Asn Val Asp His Lys Pro
        195                 200                 205
Ser Asn Thr Lys Val Asp Lys Arg Val Ala Ala Ala Cys Ala Pro Glu
    210                 215                 220
Phe Arg Arg Gly Pro Ser Val Phe Leu Phe Pro Lys Pro Lys Asp
225                 230                 235                 240
Thr Leu Met Ile Ser Arg Thr Pro Glu Val Thr Cys Val Val Val Asp
                245                 250                 255
Val Ser Gln Glu Asp Pro Glu Val Gln Phe Asn Trp Tyr Val Asp Gly
            260                 265                 270
Val Glu Val His Asn Ala Lys Thr Lys Pro Arg Glu Glu Gln Tyr Asn
        275                 280                 285
Ser Thr Tyr Arg Val Val Ser Val Leu Thr Val Leu His Gln Asp Trp
    290                 295                 300
Leu Asn Gly Lys Glu Tyr Lys Cys Lys Val Ser Asn Lys Gly Leu Pro
305                 310                 315                 320
Ser Ser Ile Glu Lys Thr Ile Ser Lys Ala Lys Gly Gln Pro Arg Glu
                325                 330                 335
Pro Gln Val Tyr Thr Leu Pro Pro Ser Gln Cys Glu Met Thr Lys Asn
            340                 345                 350
Gln Val Ser Leu Ser Cys Ala Val Lys Gly Phe Tyr Pro Ser Asp Ile
        355                 360                 365
Ala Val Glu Trp Glu Ser Asn Gly Gln Pro Glu Asn Asn Tyr Lys Thr
    370                 375                 380
Thr Pro Pro Val Leu Asp Ser Asp Gly Ser Phe Phe Leu Val Ser Arg
385                 390                 395                 400
Leu Thr Val Asp Lys Ser Arg Trp Gln Glu Gly Asn Val Phe Ser Cys
                405                 410                 415
Ser Val Met His Glu Ala Leu His Asn His Tyr Thr Gln Lys Ser Leu
            420                 425                 430
Ser Leu Ser Pro
        435
```

<210> SEQ ID NO 28
<211> LENGTH: 4
<212> TYPE: PRT
<213> ORGANISM: Artificial Sequence
<220> FEATURE:
<223> OTHER INFORMATION: An artificially synthesized peptide sequence

<400> SEQUENCE: 28

Ala Ala Ala Cys
1

<210> SEQ ID NO 29
<211> LENGTH: 214
<212> TYPE: PRT
<213> ORGANISM: Artificial Sequence
<220> FEATURE:
<223> OTHER INFORMATION: An artificially synthesized peptide sequence

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asn Ile Glu Arg Gln
            20                  25                  30

Leu Ala Trp Tyr Gln Gln Lys Pro Gly Gln Ala Pro Glu Leu Leu Ile
        35                  40                  45

Tyr Gln Ala Ser Arg Lys Glu Ser Gly Val Pro Asp Arg Phe Ser Gly
    50                  55                  60

Ser Arg Tyr Gly Thr Asp Phe Thr Leu Thr Ile Ser Ser Leu Gln Pro
65                  70                  75                  80

Glu Asp Ile Ala Thr Tyr Tyr Cys Gln Gln Tyr Ser Asp Pro Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Cys Glu
    210

<210> SEQ ID NO 30
<211> LENGTH: 215
<212> TYPE: PRT
<213> ORGANISM: Artificial Sequence
<220> FEATURE:
<223> OTHER INFORMATION: An artificially synthesized peptide sequence

<400> SEQUENCE: 30

Asp Ile Gln Met Thr Gln Ser Pro Ser Ser Leu Ser Ala Ser Val Gly
1               5                   10                  15

```
Asp Arg Val Thr Ile Thr Cys Lys Ala Ser Arg Asn Ile Glu Arg Gln
            20                  25                  30

Leu Ala Trp Tyr Gln Gln Lys Pro Gly Gln Ala Pro Glu Leu Leu Ile
        35                  40                  45

Tyr Gln Ala Ser Arg Lys Glu Ser Gly Val Pro Asp Arg Phe Ser Gly
 50                  55                  60

Ser Arg Tyr Gly Thr Asp Phe Thr Leu Thr Ile Ser Ser Leu Gln Pro
65                   70                  75                  80

Glu Asp Ile Ala Thr Tyr Tyr Cys Gln Gln Tyr Ser Asp Pro Pro Leu
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Gly Cys
210                 215

<210> SEQ ID NO 31
<211> LENGTH: 216
<212> TYPE: PRT
<213> ORGANISM: Artificial Sequence
<220> FEATURE:
<223> OTHER INFORMATION: An artificially synthesized peptide sequence

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asn Ile Glu Arg Gln
            20                  25                  30

Leu Ala Trp Tyr Gln Gln Lys Pro Gly Gln Ala Pro Glu Leu Leu Ile
        35                  40                  45

Tyr Gln Ala Ser Arg Lys Glu Ser Gly Val Pro Asp Arg Phe Ser Gly
 50                  55                  60

Ser Arg Tyr Gly Thr Asp Phe Thr Leu Thr Ile Ser Ser Leu Gln Pro
65                   70                  75                  80

Glu Asp Ile Ala Thr Tyr Tyr Cys Gln Gln Tyr Ser Asp Pro Pro Leu
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160
```

-continued

```
Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

Phe Asn Arg Gly Glu Gly Gly Cys
    210                 215

<210> SEQ ID NO 32
<211> LENGTH: 24
<212> TYPE: PRT
<213> ORGANISM: Artificial Sequence
<220> FEATURE:
<223> OTHER INFORMATION: An artificially synthesized peptide sequence

<400> SEQUENCE: 32

Lys Arg Val Glu Ser Lys Tyr Gly Pro Pro Cys Pro Pro Cys Pro Ala
1               5                   10                  15

Pro Glu Phe Arg Arg Gly Pro Ser
            20

<210> SEQ ID NO 33
<211> LENGTH: 23
<212> TYPE: PRT
<213> ORGANISM: Artificial Sequence
<220> FEATURE:
<223> OTHER INFORMATION: An artificially synthesized peptide sequence

<400> SEQUENCE: 33

Lys Arg Val Glu Ser Lys Tyr Gly Pro Cys Pro Pro Cys Pro Ala Pro
1               5                   10                  15

Glu Phe Arg Arg Gly Pro Ser
            20

<210> SEQ ID NO 34
<211> LENGTH: 22
<212> TYPE: PRT
<213> ORGANISM: Artificial Sequence
<220> FEATURE:
<223> OTHER INFORMATION: An artificially synthesized peptide sequence

<400> SEQUENCE: 34

Lys Arg Val Glu Ser Lys Tyr Gly Cys Pro Pro Cys Pro Ala Pro Glu
1               5                   10                  15

Phe Arg Arg Gly Pro Ser
            20

<210> SEQ ID NO 35
<211> LENGTH: 21
<212> TYPE: PRT
<213> ORGANISM: Artificial Sequence
<220> FEATURE:
<223> OTHER INFORMATION: An artificially synthesized peptide sequence

<400> SEQUENCE: 35

Lys Arg Val Glu Ser Lys Pro Cys Pro Pro Cys Pro Ala Pro Glu Phe
1               5                   10                  15

Arg Arg Gly Pro Ser
            20

<210> SEQ ID NO 36
<211> LENGTH: 22
```

```
<212> TYPE: PRT
<213> ORGANISM: Artificial Sequence
<220> FEATURE:
<223> OTHER INFORMATION: An artificially synthesized peptide sequence

<400> SEQUENCE: 36

Lys Arg Val Glu Ser Lys Pro Pro Cys Pro Pro Cys Pro Ala Pro Glu
1               5                   10                  15

Phe Arg Arg Gly Pro Ser
            20

<210> SEQ ID NO 37
<211> LENGTH: 23
<212> TYPE: PRT
<213> ORGANISM: Artificial Sequence
<220> FEATURE:
<223> OTHER INFORMATION: An artificially synthesized peptide sequence

<400> SEQUENCE: 37

Lys Arg Val Glu Ser Lys Pro Pro Pro Cys Pro Cys Pro Ala Pro
1               5                   10                  15

Glu Phe Arg Arg Gly Pro Ser
            20

<210> SEQ ID NO 38
<211> LENGTH: 24
<212> TYPE: PRT
<213> ORGANISM: Artificial Sequence
<220> FEATURE:
<223> OTHER INFORMATION: An artificially synthesized peptide sequence

<400> SEQUENCE: 38

Lys Arg Val Glu Ser Lys Pro Pro Pro Cys Pro Pro Cys Pro Ala
1               5                   10                  15

Pro Glu Phe Arg Arg Gly Pro Ser
            20

<210> SEQ ID NO 39
<211> LENGTH: 24
<212> TYPE: PRT
<213> ORGANISM: Artificial Sequence
<220> FEATURE:
<223> OTHER INFORMATION: An artificially synthesized peptide sequence

<400> SEQUENCE: 39

Lys Arg Val Glu Ser Lys Gly Gly Pro Pro Cys Pro Cys Pro Ala
1               5                   10                  15

Pro Glu Phe Arg Arg Gly Pro Ser
            20

<210> SEQ ID NO 40
<211> LENGTH: 24
<212> TYPE: PRT
<213> ORGANISM: Artificial Sequence
<220> FEATURE:
<223> OTHER INFORMATION: An artificially synthesized peptide sequence

<400> SEQUENCE: 40

Lys Arg Val Glu Ser Lys Pro Gly Pro Pro Cys Pro Pro Cys Pro Ala
1               5                   10                  15

Pro Glu Phe Arg Arg Gly Pro Ser
            20

<210> SEQ ID NO 41
```

```
<211> LENGTH: 24
<212> TYPE: PRT
<213> ORGANISM: Artificial Sequence
<220> FEATURE:
<223> OTHER INFORMATION: An artificially synthesized peptide sequence

<400> SEQUENCE: 41

Lys Arg Val Glu Ser Lys Tyr Tyr Pro Pro Cys Pro Pro Cys Pro Ala
1               5                   10                  15

Pro Glu Phe Arg Arg Gly Pro Ser
            20

<210> SEQ ID NO 42
<211> LENGTH: 24
<212> TYPE: PRT
<213> ORGANISM: Artificial Sequence
<220> FEATURE:
<223> OTHER INFORMATION: An artificially synthesized peptide sequence

<400> SEQUENCE: 42

Lys Arg Val Glu Ser Lys Tyr Pro Pro Cys Pro Pro Cys Pro Ala
1               5                   10                  15

Pro Glu Phe Arg Arg Gly Pro Ser
            20

<210> SEQ ID NO 43
<211> LENGTH: 24
<212> TYPE: PRT
<213> ORGANISM: Artificial Sequence
<220> FEATURE:
<223> OTHER INFORMATION: An artificially synthesized peptide sequence

<400> SEQUENCE: 43

Lys Arg Val Glu Ser Lys Tyr Gly Tyr Pro Cys Pro Pro Cys Pro Ala
1               5                   10                  15

Pro Glu Phe Arg Arg Gly Pro Ser
            20

<210> SEQ ID NO 44
<211> LENGTH: 24
<212> TYPE: PRT
<213> ORGANISM: Artificial Sequence
<220> FEATURE:
<223> OTHER INFORMATION: An artificially synthesized peptide sequence

<400> SEQUENCE: 44

Lys Arg Val Glu Ser Lys Tyr Gly Gly Pro Cys Pro Pro Cys Pro Ala
1               5                   10                  15

Pro Glu Phe Arg Arg Gly Pro Ser
            20

<210> SEQ ID NO 45
<211> LENGTH: 24
<212> TYPE: PRT
<213> ORGANISM: Artificial Sequence
<220> FEATURE:
<223> OTHER INFORMATION: An artificially synthesized peptide sequence

<400> SEQUENCE: 45

Lys Arg Val Glu Ser Lys Tyr Gly Pro Tyr Cys Pro Pro Cys Pro Ala
1               5                   10                  15

Pro Glu Phe Arg Arg Gly Pro Ser
            20
```

```
<210> SEQ ID NO 46
<211> LENGTH: 24
<212> TYPE: PRT
<213> ORGANISM: Artificial Sequence
<220> FEATURE:
<223> OTHER INFORMATION: An artificially synthesized peptide sequence

<400> SEQUENCE: 46

Lys Arg Val Glu Ser Lys Tyr Gly Pro Gly Cys Pro Pro Cys Pro Ala
1               5                   10                  15

Pro Glu Phe Arg Arg Gly Pro Ser
            20

<210> SEQ ID NO 47
<211> LENGTH: 24
<212> TYPE: PRT
<213> ORGANISM: Artificial Sequence
<220> FEATURE:
<223> OTHER INFORMATION: An artificially synthesized peptide sequence

<400> SEQUENCE: 47

Lys Arg Val Glu Ser Lys Tyr Pro Gly Pro Cys Pro Pro Cys Pro Ala
1               5                   10                  15

Pro Glu Phe Arg Arg Gly Pro Ser
            20

<210> SEQ ID NO 48
<211> LENGTH: 24
<212> TYPE: PRT
<213> ORGANISM: Artificial Sequence
<220> FEATURE:
<223> OTHER INFORMATION: An artificially synthesized peptide sequence

<400> SEQUENCE: 48

Lys Arg Val Glu Ser Lys Tyr Pro Pro Gly Cys Pro Pro Cys Pro Ala
1               5                   10                  15

Pro Glu Phe Arg Arg Gly Pro Ser
            20

<210> SEQ ID NO 49
<211> LENGTH: 24
<212> TYPE: PRT
<213> ORGANISM: Artificial Sequence
<220> FEATURE:
<223> OTHER INFORMATION: An artificially synthesized peptide sequence

<400> SEQUENCE: 49

Lys Arg Val Glu Ser Lys Gly Tyr Pro Pro Cys Pro Pro Cys Pro Ala
1               5                   10                  15

Pro Glu Phe Arg Arg Gly Pro Ser
            20

<210> SEQ ID NO 50
<211> LENGTH: 24
<212> TYPE: PRT
<213> ORGANISM: Artificial Sequence
<220> FEATURE:
<223> OTHER INFORMATION: An artificially synthesized peptide sequence

<400> SEQUENCE: 50

Lys Arg Val Glu Ser Lys Gly Pro Tyr Pro Cys Pro Pro Cys Pro Ala
1               5                   10                  15

Pro Glu Phe Arg Arg Gly Pro Ser
            20
```

<210> SEQ ID NO 51
<211> LENGTH: 24
<212> TYPE: PRT
<213> ORGANISM: Artificial Sequence
<220> FEATURE:
<223> OTHER INFORMATION: An artificially synthesized peptide sequence

<400> SEQUENCE: 51

Lys Arg Val Glu Ser Lys Gly Pro Pro Tyr Cys Pro Pro Cys Pro Ala
1               5                   10                  15

Pro Glu Phe Arg Arg Gly Pro Ser
            20

<210> SEQ ID NO 52
<211> LENGTH: 24
<212> TYPE: PRT
<213> ORGANISM: Artificial Sequence
<220> FEATURE:
<223> OTHER INFORMATION: An artificially synthesized peptide sequence

<400> SEQUENCE: 52

Lys Arg Val Glu Ser Lys Pro Tyr Gly Pro Cys Pro Pro Cys Pro Ala
1               5                   10                  15

Pro Glu Phe Arg Arg Gly Pro Ser
            20

<210> SEQ ID NO 53
<211> LENGTH: 24
<212> TYPE: PRT
<213> ORGANISM: Artificial Sequence
<220> FEATURE:
<223> OTHER INFORMATION: An artificially synthesized peptide sequence

<400> SEQUENCE: 53

Lys Arg Val Glu Ser Lys Pro Tyr Pro Gly Cys Pro Pro Cys Pro Ala
1               5                   10                  15

Pro Glu Phe Arg Arg Gly Pro Ser
            20

<210> SEQ ID NO 54
<211> LENGTH: 24
<212> TYPE: PRT
<213> ORGANISM: Artificial Sequence
<220> FEATURE:
<223> OTHER INFORMATION: An artificially synthesized peptide sequence

<400> SEQUENCE: 54

Lys Arg Val Glu Ser Lys Pro Gly Tyr Pro Cys Pro Pro Cys Pro Ala
1               5                   10                  15

Pro Glu Phe Arg Arg Gly Pro Ser
            20

<210> SEQ ID NO 55
<211> LENGTH: 24
<212> TYPE: PRT
<213> ORGANISM: Artificial Sequence
<220> FEATURE:
<223> OTHER INFORMATION: An artificially synthesized peptide sequence

<400> SEQUENCE: 55

Lys Arg Val Glu Ser Lys Pro Gly Pro Tyr Cys Pro Pro Cys Pro Ala
1               5                   10                  15

Pro Glu Phe Arg Arg Gly Pro Ser
            20

```
<210> SEQ ID NO 56
<211> LENGTH: 24
<212> TYPE: PRT
<213> ORGANISM: Artificial Sequence
<220> FEATURE:
<223> OTHER INFORMATION: An artificially synthesized peptide sequence

<400> SEQUENCE: 56

Lys Arg Val Glu Ser Lys Pro Pro Tyr Gly Cys Pro Pro Cys Pro Ala
1               5                   10                  15

Pro Glu Phe Arg Arg Gly Pro Ser
            20

<210> SEQ ID NO 57
<211> LENGTH: 24
<212> TYPE: PRT
<213> ORGANISM: Artificial Sequence
<220> FEATURE:
<223> OTHER INFORMATION: An artificially synthesized peptide sequence

<400> SEQUENCE: 57

Lys Arg Val Glu Ser Lys Pro Pro Gly Tyr Cys Pro Pro Cys Pro Ala
1               5                   10                  15

Pro Glu Phe Arg Arg Gly Pro Ser
            20

<210> SEQ ID NO 58
<211> LENGTH: 24
<212> TYPE: PRT
<213> ORGANISM: Artificial Sequence
<220> FEATURE:
<223> OTHER INFORMATION: An artificially synthesized peptide sequence

<400> SEQUENCE: 58

Lys Arg Val Glu Ser Lys Tyr Cys Pro Pro Cys Pro Pro Cys Pro Ala
1               5                   10                  15

Pro Glu Phe Arg Arg Gly Pro Ser
            20

<210> SEQ ID NO 59
<211> LENGTH: 16
<212> TYPE: PRT
<213> ORGANISM: Artificial Sequence
<220> FEATURE:
<223> OTHER INFORMATION: An artificially synthesized peptide sequence

<400> SEQUENCE: 59

Lys Arg Val Ala Ala Ala Cys Ala Pro Glu Phe Arg Arg Gly Pro Ser
1               5                   10                  15

<210> SEQ ID NO 60
<211> LENGTH: 12
<212> TYPE: PRT
<213> ORGANISM: Artificial Sequence
<220> FEATURE:
<223> OTHER INFORMATION: An artificially synthesized peptide sequence

<400> SEQUENCE: 60

Lys Arg Val Ala Pro Glu Phe Arg Arg Gly Pro Ser
1               5                   10

<210> SEQ ID NO 61
<211> LENGTH: 18
<212> TYPE: PRT
```

```
<213> ORGANISM: Artificial Sequence
<220> FEATURE:
<223> OTHER INFORMATION: An artificially synthesized peptide sequence

<400> SEQUENCE: 61

Lys Arg Val Pro Cys Pro Pro Cys Pro Ala Pro Glu Phe Arg Arg Gly
1               5                   10                  15

Pro Ser

<210> SEQ ID NO 62
<211> LENGTH: 24
<212> TYPE: PRT
<213> ORGANISM: Artificial Sequence
<220> FEATURE:
<223> OTHER INFORMATION: An artificially synthesized peptide sequence

<400> SEQUENCE: 62

Lys Arg Val Glu Ser Lys Tyr Gly Pro Pro Cys Pro Val Pro Pro Pro
1               5                   10                  15

Pro Pro Cys Cys His Pro Pro Ser
            20

<210> SEQ ID NO 63
<211> LENGTH: 31
<212> TYPE: PRT
<213> ORGANISM: Artificial Sequence
<220> FEATURE:
<223> OTHER INFORMATION: An artificially synthesized peptide sequence

<400> SEQUENCE: 63

Lys Arg Val Glu Ser Lys Ser Cys Asp Thr Pro Pro Pro Cys Pro Arg
1               5                   10                  15

Cys Pro Gly Pro Ser Val Ala Pro Glu Phe Arg Arg Gly Pro Ser
            20                  25                  30

<210> SEQ ID NO 64
<211> LENGTH: 24
<212> TYPE: PRT
<213> ORGANISM: Artificial Sequence
<220> FEATURE:
<223> OTHER INFORMATION: An artificially synthesized peptide sequence

<400> SEQUENCE: 64

Lys Arg Val Glu Pro Lys Ser Cys Asp Lys Cys Pro Pro Cys Pro Ala
1               5                   10                  15

Pro Glu Phe Arg Arg Gly Pro Ser
            20

<210> SEQ ID NO 65
<211> LENGTH: 26
<212> TYPE: PRT
<213> ORGANISM: Artificial Sequence
<220> FEATURE:
<223> OTHER INFORMATION: An artificially synthesized peptide sequence

<400> SEQUENCE: 65

Lys Arg Val Glu Pro Lys Ser Cys Asp Thr His Thr Cys Pro Pro Cys
1               5                   10                  15

Pro Ala Pro Glu Phe Arg Arg Gly Pro Ser
            20                  25

<210> SEQ ID NO 66
<211> LENGTH: 25
<212> TYPE: PRT
```

```
<213> ORGANISM: Artificial Sequence
<220> FEATURE:
<223> OTHER INFORMATION: An artificially synthesized peptide sequence

<400> SEQUENCE: 66

Lys Arg Val Glu Pro Lys Ser Cys Thr His Thr Cys Pro Pro Cys Pro
1               5                   10                  15

Ala Pro Glu Phe Arg Arg Gly Pro Ser
            20                  25

<210> SEQ ID NO 67
<211> LENGTH: 23
<212> TYPE: PRT
<213> ORGANISM: Artificial Sequence
<220> FEATURE:
<223> OTHER INFORMATION: An artificially synthesized peptide sequence

<400> SEQUENCE: 67

Lys Arg Val Glu Pro Cys Thr His Thr Cys Pro Pro Cys Pro Ala Pro
1               5                   10                  15

Glu Phe Arg Arg Gly Pro Ser
            20

<210> SEQ ID NO 68
<211> LENGTH: 20
<212> TYPE: PRT
<213> ORGANISM: Artificial Sequence
<220> FEATURE:
<223> OTHER INFORMATION: An artificially synthesized peptide sequence

<400> SEQUENCE: 68

Lys Arg Pro Pro Pro Pro Cys Pro Pro Cys Pro Ala Pro Glu Phe Arg
1               5                   10                  15

Arg Gly Pro Ser
            20

<210> SEQ ID NO 69
<211> LENGTH: 20
<212> TYPE: PRT
<213> ORGANISM: Artificial Sequence
<220> FEATURE:
<223> OTHER INFORMATION: An artificially synthesized peptide sequence

<400> SEQUENCE: 69

Lys Arg Val Ala Ala Ala Cys Pro Pro Cys Pro Ala Pro Glu Phe Arg
1               5                   10                  15

Arg Gly Pro Ser
            20

<210> SEQ ID NO 70
<211> LENGTH: 15
<212> TYPE: PRT
<213> ORGANISM: Artificial Sequence
<220> FEATURE:
<223> OTHER INFORMATION: An artificially synthesized peptide sequence

<400> SEQUENCE: 70

Lys Arg Val Ala Ala Cys Ala Pro Glu Phe Arg Arg Gly Pro Ser
1               5                   10                  15

<210> SEQ ID NO 71
<211> LENGTH: 17
<212> TYPE: PRT
<213> ORGANISM: Artificial Sequence
<220> FEATURE:
```

```
<223> OTHER INFORMATION: An artificially synthesized peptide sequence

<400> SEQUENCE: 71

Lys Arg Val Ala Ala Ala Ala Cys Ala Pro Glu Phe Arg Arg Gly Pro
1               5                   10                  15

Ser

<210> SEQ ID NO 72
<211> LENGTH: 21
<212> TYPE: PRT
<213> ORGANISM: Artificial Sequence
<220> FEATURE:
<223> OTHER INFORMATION: An artificially synthesized peptide sequence

<400> SEQUENCE: 72

Lys Arg Val Pro Pro Pro Pro Cys Pro Pro Cys Pro Ala Pro Glu Phe
1               5                   10                  15

Arg Arg Gly Pro Ser
            20

<210> SEQ ID NO 73
<211> LENGTH: 18
<212> TYPE: PRT
<213> ORGANISM: Artificial Sequence
<220> FEATURE:
<223> OTHER INFORMATION: An artificially synthesized peptide sequence

<400> SEQUENCE: 73

Lys Arg Val Ala Cys Pro Pro Cys Pro Ala Pro Glu Phe Arg Arg Gly
1               5                   10                  15

Pro Ser

<210> SEQ ID NO 74
<211> LENGTH: 20
<212> TYPE: PRT
<213> ORGANISM: Artificial Sequence
<220> FEATURE:
<223> OTHER INFORMATION: An artificially synthesized peptide sequence

<400> SEQUENCE: 74

Lys Arg Val Gly Gly Gly Cys Pro Pro Cys Pro Ala Pro Glu Phe Arg
1               5                   10                  15

Arg Gly Pro Ser
            20

<210> SEQ ID NO 75
<211> LENGTH: 16
<212> TYPE: PRT
<213> ORGANISM: Artificial Sequence
<220> FEATURE:
<223> OTHER INFORMATION: An artificially synthesized peptide sequence

<400> SEQUENCE: 75

Lys Arg Val Gly Gly Gly Cys Ala Pro Glu Phe Arg Arg Gly Pro Ser
1               5                   10                  15
```